(12) United States Patent
Baker et al.

US008394914B2

(10) Patent No.: US 8,394,914 B2
(45) Date of Patent: *Mar. 12, 2013

(54) FUNCTIONAL POLYGLYCOLIDE NANOPARTICLES DERIVED FROM UNIMOLECULAR MICELLES

(75) Inventors: Gregory L. Baker, Haslett, MI (US); Milton R. Smith, III, East Lansing, MI (US); Erin Vogel, Midland, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 488 days.

This patent is subject to a terminal disclaimer.

(21) Appl. No.: 12/460,655

(22) Filed: Jul. 22, 2009

(65) Prior Publication Data
US 2009/0325292 A1 Dec. 31, 2009

Related U.S. Application Data

(63) Continuation-in-part of application No. 12/229,544, filed on Aug. 25, 2008.

(60) Provisional application No. 61/135,679, filed on Jul. 23, 2008, provisional application No. 60/966,042, filed on Aug. 24, 2007.

(51) Int. Cl.
*C08G 63/08* (2006.01)
(52) U.S. Cl. ..................................................... 528/354
(58) Field of Classification Search .................. 435/375; 424/400; 528/354, 271
See application file for complete search history.

(56) References Cited

U.S. PATENT DOCUMENTS

| | | | |
|---|---|---|---|
| 5,625,030 A | 4/1997 | Williams et al. | |
| 6,469,133 B2 * | 10/2002 | Baker et al. | 528/354 |
| 7,375,234 B2 | 5/2008 | Sharpless et al. | |
| 7,763,736 B2 | 7/2010 | Sharpless et al. | |
| 2001/0044514 A1 | 11/2001 | Baker et al. | |
| 2002/0155092 A1 | 10/2002 | Leong et al. | |
| 2005/0201972 A1 | 9/2005 | Seo et al. | |
| 2006/0188486 A1 | 8/2006 | Carpenter et al. | |
| 2007/0020620 A1 | 1/2007 | Finn et al. | |
| 2007/0141363 A1 | 6/2007 | Acosta et al. | |
| 2008/0311412 A1 | 12/2008 | Fokin et al. | |
| 2009/0054619 A1 | 2/2009 | Baker et al. | |
| 2009/0069561 A1 | 3/2009 | Fokin et al. | |
| 2009/0181402 A1 | 7/2009 | Finn et al. | |
| 2009/0182151 A1 | 7/2009 | Wu et al. | |
| 2009/0306310 A1 | 12/2009 | Wu et al. | |
| 2010/0286405 A1 | 11/2010 | Fokin et al. | |

OTHER PUBLICATIONS

Parrish et al "PEG- and Peptide-Grafted Aliphatic Polyesters by Click Chemistry", JACS, 7404-7410, published on Web on Apr. 29, 2005.*
Liu, Y. Y.; Miyoshi, H.; Nakamura, M. Int. J. Cancer 2007, 120, 2527-2537.
Couvreur, P.; Puisieux, F. Adv. Drug Deliv. Rev. 1993, 10, 141-162.
Duncan, R. Nat. Rev. Drug Discov. 2003, 2, 347-360.
Jin, S.; Ye, K. M. 2007, 23, 32-41.
Hawker, C. J.; Wooley, K. L. Science 2005, 309, 1200-1205.
Newkome, G. R.; Moorefield, C. N.; Baker, G. R.; Saunders, M. J.; Grossman, S. H. Angew. Chem.-Int. Edit. Engl. 1991, 30, 1178-1180.
Lawrence, M. J. Chem. Soc. Rev. 1994, 23, 417-424.
Wooley, K. L. J. Polym. Sci. Pol. Chem. 2000, 38, 1397-1407.
Kataoka, K.; Harada, A.; Nagasaki, Y. Adv. Drug Deliv. Rev. 2001, 47, 113-131.
Emoto, K.; Iijima, M.; Nagasaki, Y.; Kataoka, K. J. Am. Chem. Soc. 2000, 122, 2653-2654.
Butun, V.; Lowe, A. B.; Billingham, N. C.; Armes, S. P. J. Am. Chem. Soc. 1999, 121, 4288-4289.
Iijima, M.; Nagasaki, Y.; Okada, T.; Kato, M.; Kataoka, K. Macromolecules 1999, 32, 1140-1146.
Butun, V.; Billingham, N. C.; Armes, S. P. J. Am. Chem. Soc. 1998, 120, 12135-12136.
Schartl, W. Adv. Mater. 2000, 12, 1899-+.
O'Reilly, R. K.; Joralemon, M. J.; Wooley, K. L.; Hawker, C. J. Chem. Mat. 2005, 17, 5976-5988.
Joralemon, M. J.; O'Reilly, R. K.; Hawker, C. J.; Wooley, K. L. J. Am. Chem. Soc. 2005, 127, 16892-16899.
Blomberg, S.; Ostberg, S.; Harth, E.; Bosman, A. W.; Van Horn, B.; Hawker, C. J. J. Polym. Sci. Pol. Chem. 2002, 40, 1309-1320.
Harth, E.; Van Horn, B.; Lee, V. Y.; Germack, D. S.; Gonzales, C. P.; Miller, R. D.; Hawker, C. J. J. Am. Chem. Soc. 2002, 124, 8653-8660.
Croce, T. A.; Hamilton, S. K.; Chen, M. L.; Muchalski, H.; Harth, E. Macromolecules 2007, 40, 6028-6031.
Jiang, X.; Vogel, E.; Baker, G. L.; Smith, M. R., III J. Polym. Sci., Part A, Polym. Chem. 2007, 45, 5227-5236.
Jing, F.; Smith, M. R., III; Baker, G. L. Macromolecules 2007, 40, (in press, DOI:10.1021/ma071430d).
Liu, T. Q.; Simmons, T. L.; Bohnsack, D. A.; Mackay, M. E.; Smith, M. R., III; Baker, G. L. Macromolecules 2007, 40, 6040-6047.
Yin, M.; Baker, G. L. Macromolecules 1999, 32, 7711-7718.
Simmons, T. L.; Baker, G. L. Biomacromolecules 2001, 2, 658-663.
Jiang, X.; Smith, M. R., III; Baker, G. L., (in press, DOI: 10.1021/ma070775t).
Jiang, X.; Vogel, E. B.; Milton R. Smith, I.; Baker, G. L. Macromolecules 2008, 41, 1937-1944.
Sivakumar, K.; Xie, F.; Cash, B. M.; Long, S.; Barnhill, H. N.; Wang, Q. Org. Lett. 2004, 6, 4603-4606.

(Continued)

*Primary Examiner* — Gregory Listvoyb
(74) *Attorney, Agent, or Firm* — Harness, Dickey & Pierce, P.L.C.

(57) ABSTRACT

Poly(glycolide) polymers are disclosed. The polymers generally include a glycolide-based polymer backbone that includes one or more functional groups such as alkynyl groups, hydrophilic organic triazole groups, hydrophobic organic triazole groups (also including amphiphilic organic triazole groups), di-triazole organic crosslinking groups, and triazole-substituted drug derivatives. The alkynyl groups provide reactive sites for further functionalization of the polymer, for example by reaction with azide derivatives. The polymers can further encapsulate a drug for delivery to a patient (i.e., as compared to drug derivatives that are covalently attached to the polymer). The polymers can be in the form of thermodynamically stable unimolecular micelles or crosslinked nanoparticles. The polymer compositions are completely biodegradable and hold great potential for use in biomedical applications.

10 Claims, 12 Drawing Sheets

OTHER PUBLICATIONS

Uhrich, K. E.; Cannizzaro, S. M.; Langer, R. S.; Shakesheff, K. M. 1999, 99, 3181-3198.

Adams et al., Amphiphilic Block Copolymers for Drug Delivery, J. Pharm. Sci. 92(7):1343-1355, May 2003.

Aoshima et al., Synthesis of thermally-induced phase separating polymer with well-defined polymer structure by living cationic polymerization. I. Synthesis of poly(vinyl ether)s with oxyethylene units in the pendant and its phase separation behavior in aqueous solution, Journal of Polymer Science: Part A: Polymer Chemistry 30(11):2407-2413 (1992).

Bala et al., PLGA Nanoparticles in Drug Delivery: The State of the Art, 21(5):387-422 (2004).

Becker et al., Diblock Copolymers, Micelles, and Shell-Crosslinked Nanoparticles Containing Poly(4-fluorostyrene): Tools for Detailed Analyses of Nanostructured Materials, Journal of Polymer Science: Part A: Polymer Chemistry 39:4152-4166 (2001).

Benabdillah et al., Synthesis and Characterization of Novel Degradable Polyesters Derived from D-Gluconic and Glycolic Acids, Macromolecules 32:8774-8780 (1999).

Bhattarai et al., Novel Polymeric Micelles of Amphiphilic Triblock Copolymer Poly(p-Dioxanone-co-L-Lactide)-block-Poly(ethylene glycol), Pharm. Res. 20(12):2021-2027 (2003).

Binder et al., 'Click' Chemistry in Polymer and Materials Science, Macromol. Rapid Commun. 28:15-24 (2007).

Bohlmann et al., Polyacetylenverbindungen 30. Synthese von Natürlich Vorkommenden Polyacetylenverbindungen mit Endständigen Dreifachbindungen, Chemische BerichteRecueil 94(4):948-957 (1961).

Chapman et al., Hydraamphiphiles: Novel Linear Dendritic Block Copolymer Surfactants, J. Am. Chem. Soc. 116:11195-11196 (1994).

Cho et al., Chondrogenic differentiation of human mesenchymal stem cells using a thermosensitive poly(N-isopropylacrylamide) and water-soluble chitosan copolymer, Biomaterials 25(26):5743-5751 (2004).

Diaz et al., Click Chemistry in Materials Synthesis. 1. Adhesive Polymers from Copper-Catalyzed Azide-Alkyne Cycloaddition, J. Polymer Science: Part A: Polymer Chemistry 42:4392-4403 (2004).

Dirks et al., Preparation of Biohybrid Amphiphiles via the Copper Catalysed Huisgen [3 +2] Dipolar Cycloaddition Reaction, Chem. Commun. 4172-4174 (2005).

Emoto et al., Coating of Surfaces with Stabilized Reactive Micelles from Poly(ethylene glycol)-Poly(DL-lactic acid) Block Copolymer, Langmuir 15:5212-5218 (1999).

Englert et al., Click Chemistry as a Powerful Tool for the Construction of Functional Poly(p-phenyleneethynylene)s: Comparison of Pre-and Postfunctionalization Schemes, Macromolecules 38:5868-5877 (2005).

Frey et al., Dendritic Polyols Based on Carbosilanes—Lipophilic Dendrimers With Hydrophilic Skin, Macromol. Symp. 102:19-26 (1996).

Gao et al., Gradient Polymer Elution Chromatographic Analysis of alpha,omega-Dihydroxypolystyrene Synthesized via ATRP and Click Chemistry, Macromolecules 38:8979-8982 (2005).

Gil et al., Stimuli-responsive polymers and their bioconjugates, Progress in Polymer Science 29(12):1173-1222 (2004).

Gonsalves et al., Synthesis and surface characterization of funtionalized polylactide copolymer microparticles, Biomaterials 19(16):1501-1505 (1998).

Gref et al., Biodegradable Long-Circulating Polymeric Nanospheres, Science 263:1600-1603 (1994).

Gref et al., The controlled intravenous delivery of drugs using PEG-coated sterically stabilized nanospheres, Adv. Drug Deliv. Rev. 16:215-233 (1995).

Han et al., Synthesis of thermally sensitive water-soluble polymethacrylates by living anionic polymerization of oligo(ethylene glycol) methyl ether methacrylates, Macromolecules 36(22):8312-8319 (2003).

Hasirci et al., Nanobiomaterials: a review of the existing science and technology, and new approaches, Journal of Biomaterials Science-Polymer Edition 17(11):1241-1268 (2006).

Huh et al., Synthesis and characterization of poly(ethylene glycol)/poly(L-lactic acid) alternating multiblock copolymers, Polymer 40(22):6147-6155 (1999).

Jiang et al., Synthesis and Polymerization of a Novel Amphiphilic Lactide Monomer, Polymer Preprints 46(2):1040 (2005).

Joralemon et al., Dendrimers Clicked Together Divergently, Macromolecules 38:5436-5443 (2005).

Kakizawa et al., Block copolymer micelles for delivery of gene and related compounds, Adv. Drug Deliv. Rev. 54:203-222 (2002).

Kidchob et al., Thermo-responsive microcapsules using poly(N-isopropylacrylamide), Kobunshi Ronbunshu 55(4):192-199 (1998).

Kim et al., Core-stabilized Polymeric Micelle as Potential Drug Carrier: Increased Solubilization of Taxol, Polym. Adv. Technol. 10:647-654 (1999).

Kimura et al., Ring-Opening Polymerization of 3(S)-[(Benzyloxycarbonyl)methyl]-1,4-dioxane-2,5-dione: a New Route to a Poly(alpha-hydroxy acid) with Pendant Carboxyl Groups, Macromolecules 21:3338-3340 (1988).

Li et al., Combination of Ring-Opening Polymerization and "Click" Chemistry for the Synthesis of an Amphiphilic Tadpole-Shaped Poly(E-Caprolactone) Grafted by PEO, Macromolecules 40:824-831 (2007).

Liu et al., Synthesis and Characterization of Biodegradable "Polystyrene" by Ring Opening Polymerization, Polymeric Materials: Science & Engineering 88:420-421 (2003).

Liu et al., Unimolecular Micelles: Synthesis and Characterization of Amphiphilic Polymer Systems, J. Polym. Sci.: Part A: Pol. Chem. 37:703-711 (1999).

Lutz et al., Combining Atom Transfer Radical Polymerization and Click Chemistry: A Versatile Method for the Preparation of End-Functional Polymers, Macromol. Rapid Commun. 26:514-518 (2005).

Lutz et al., Point by point comparison of two thermosensitive polymers exhibiting a similar LCST: Is the age of poly(NIPAM) over?, Journal of the American Chemical Society 128(40):13046-13047 (2006).

Lutz et al., Preparation of ideal PEG analogues with a tunable thermosensitivity by controlled radical copolymerization of 2-(2-methoxyethoxy)ethyl methacrylate and oligo(ethylene glycol) methacrylate, Macromolecules 39(2):893-896 (2006).

Lutz, 1,3-Dipolar Cycloadditions of Azides and Alkynes: A Universal Litigation Tool in Polymer and Materials Science, Angew. Chem. Int. Ed. 46:1018-1025 (2007).

Malkoch et al., Orthogonal Approaches to the Simultaneous and Cascade Functionalization of Macromolecules Using Click Chemistry, J. Am. Chem. Soc. 127:14942-14949 (2005).

Malkoch et al., Structurally Diverse Dendritic Libraries: A Highly Efficient Functionalization Approach Using Click Chemistry, Macromolecules 38:3663-3678 (2005).

Mecerreyes et al., Ring-Opening Polymerization of 6-Hydroxynon-8-Enoic Acid Lactone: Novel Biodegradable Copolymers Containing Allyl Pendent Groups, J. Polymer Science: Part A: Polymer Chemistry 38:870-875 (2000).

Newkome et al., Alkane Cascade Polymers Possessing Micellar Topology: Micellanoic Acid Derivatives, Angew. Chem. Int. Ed. Engl. 30(9):1176-1178 (1991).

O'Neil et al., Phosphatidylcholine-Derived Bolaamphiphiles via Click Chemistry, Organic Letters 9(2):199-202 (2007).

Opsteen et al., Modular synthesis of block copolymers via cycloaddition of terminal azide and alkyne functionalized polymers, Chem. Commun., 57-59 (2005).

Parrish et al., Aliphatic Polyesters with Pendant Cyclopentene Groups: Controlled Synthesis and Conversion to Polyester-graft-PEG Copolymers, Macromolecules 37:5863-5865 (2004).

Parrish et al., PEG- and Peptide-Grafted Aliphatic Polyesters by Click Chemistry, J. Am. Chem. Soc. 127:7404-7410 (2005).

Parrish et al., Soluble Camptothecin Derivatives Prepared by Click Cycloaddition Chemistry on Functional Aliphatic Polyesters, Bioconjugate Chem. 18:263-267 (2007).

Porjazoska et al., Synthesis and aqueous solution properties of functionalized and thermoresponsive poly(D,L-lactide)/polyether block copolymers, Macromolecular Symposia 210:427-436 (2004).

Portis et al., Confocal Microscopy for the Analysis of siRNA Delivery by Polymeric Nanoparticles, Microscopy Research and Technique 73:878-885 (2010).

Rieger et al., Lactone End-Capped Poly(ethylene oxide) as a New Building Block for Biomaterials, Macromolecules 37:9738-9745 (2004).

Riva et al., Combination of Ring-Opening Polymerization and "Click" Chemistry Towards Functionalization of Aliphatic Polyesters, Chem. Commun. 5334-5336 (2005).

Riva et al., Combination of Ring-Opening Polymerization and "Click Chemistry": Toward Functionalization and Grafting of Poly(E-caprolactone), Macromolecules 40:796-803 (2007).

Rostovtsev et al., A Stepwise Huisgen Cycloaddition Process: Copper(I)-Catalyzed Regioselective "Litigation" of Azides and Terminal Alkynes, Angew. Chem. Int. Ed. 41(14): 2596-2599 (2002).

Schacht et al., Polyacetal and poly(ortho ester)-poly(ethylene glycol) graft copolymer thermogels: Preparation, hydrolysis and FITC-BSA release studies, Journal of Controlled Release 116(2):219-225 (2006).

Schmidt et al., Preparation of Some Chiral Aminodiols from Tartaric Acid. Chiral Lithium Aluminum Hydride Derivatives for Asymmetric Ketone Reductions, Chem. Ber. 113:1691-1707 (1980).

Service, Nanoparticle Trojan Horses Gallop From the Lab Into the Clinic, Science 330:314-315 (2010).

Shimokuri et al., Specific thermosensitive volume change of biopolymer gels derived from propylated poly(gamma-glutamate)s, Journal of Polymer Science: Part A: Polymer Chemistry 42(18):4492-4501 (2004).

Skwarczynski et al., Paclitaxel prodrugs: Toward smarter delivery of anticancer agents, Journal of Medicinal Chemistry 49(25):7253-7269 (2006).

Sumerlin et al., Highly Efficient "Click" Functionalization of Poly(3-azidopropyl methacrylate) Prepared by ATRP, Macromolecules 38:7540-7545 (2005).

Tachibana et al., Thermo-and pH-responsive biodegradable poly(alpha-N-substituted gamma-glutamine)s, Biomacromolecules 4(5):1132-1134 (2003).

Tomalia et al., Starburst Dendrimers. 4. Covalently Fixed Unimolecular Assemblages Reminiscent of Spheroidal Micelles, Macromolecules 20:1164-1167 (1987).

Trollsas et al., Hydrophilic Aliphatic Polyesters: Design, Synthesis, and Ring-Opening Polymerization of Functional Cyclic Esters, Macromolecules 33:4619-4627 (2000).

Tsuda et al., The use of patterned dual thermoresponsive surfaces for the collective recovery as co-cultured cell sheets, Biomaterials 26(14):1885-1893 (2005).

van Hest et al., Polystyrene-Dendrimer Amphiphilic Block Copolymers with a Generation-Dependent Aggregation, Science 268:1592-1595 (1995).

van Hest et al., Polystyrene-Poly(propylene imine) Dendrimers: Synthesis, Characterization, and Association Behavior of a New Class of Amphiphiles, Chem. Eur. J. 2(12):1616-1626 (1996).

Vogeley et al., Synthesis and Polymerization of Derivatized Lactide Monomers, Polymer Preprints (American Chemical Society, Division of Polymer Chemistry) 46(1):336 (2005).

Watanabe et al., Preparation and physical properties of thermoresponsive biodegradable poly(asparagine) derivatives, Chemistry Letters 34(6):876-877 (2005).

Winzenburg et al., Biodegradable polymers and their potential use in parenteral veterinary drug delivery systems, Advanced Drug Delivery Reviews 56(10):1453-1466 (2004).

Wu et al., Efficiency and Fidelity in a Click-Chemistry Route to Triazole Dendrimers by the Copper(I)-Catalyzed Ligation of Azides and Alkynes, Angew. Chem. Int. Ed. 43:3928-3932 (2004).

Wu, Multivalent, bifunctional dendrimers prepared by click chemistry, Chem. Commun., 5775-5777 (2005).

Yang et al., Cell sheet engineering: Recreating tissues without biodegradable scaffolds, Biomaterials 26(33):6415-6422 (2005).

Yang et al., Thermoresponsive gelatin/monomethoxy poly(ethylene glycol)-poly(D,L-lactide) hydrogels: formulation, characterization, and antibacterial drug delivery, Pharmaceutical Research 23(1):205-214 (2006).

Zhao et al., Synthesis of thermosensitive water-soluble polystyrenics with pendant methoxyoligo(ethylene glycol) groups by nitroxide-mediated radical polymerization, Macromolecules, 38(23):9509-9517 (2005).

Zhong et al., Synthesis and aqueous phase behavior of thermoresponsive biodegradable poly(D,L-3-methylglycolide)-block-poly(ethylene glycol)-block-poly(D,L-3-methylglycolide) triblock copolymers, Macromolecular Chemistry and Physics 203(12):1797-1803 (2002).

* cited by examiner

~50 nm
a multi-polymer
vesicle or micelle

~ 15 nm
a unimolecular
micelle

US 8,394,914 B2

FUNCTIONAL POLYGLYCOLIDE NANOPARTICLES DERIVED FROM UNIMOLECULAR MICELLES

CROSS-REFERENCE TO RELATED APPLICATIONS

Priority to U.S. Provisional Application Ser. No. 61/135,679, filed Jul. 23, 2008, which is incorporated herein by reference in its entirety, is claimed.

This application is a continuation-in-part of U.S. patent application Ser. No. 12/229,544, filed Aug. 25, 2008 (Monday), which in turn claims the priority benefit of U.S. Provisional Application No. 60/966,042, filed Aug. 24, 2007, both of which are incorporated herein by reference in their entireties.

BACKGROUND OF THE DISCLOSURE

1. Field of the Disclosure

Degradable comb polymers that individually self-aggregate into unimolecular micelles in an aqueous solution are disclosed. The compositions generally include poly(glycolide) polymers having pendant alkynyl groups that can be functionalized via triazole formation with hydrophilic and other groups. The polymeric micelles can be chemically cross-linked to form organic nanoparticles that retain their chemical functionality and their degradability. The micelles are capable of hydrophobic drug encapsulation and have pendant reactive sites that can be used for cross-linking or covalent drug attachment. The micelles are completely biodegradable and can be used in biomedical applications for controlled drug release.

2. Brief Description of Related Technology

Inorganic nanoparticles have a long and rich history, having benefited from favorable physical properties such as mechanical, thermal, and chemical stability. While comparable developments in organic nanoparticles are more recent, the structural diversity of organic materials and their application to complex problems in medicine has made the synthesis and characterization of organic nanoparticles one of the most active topics in polymer science.[1]

Organic nanoparticles are important in many applications, but especially for the encapsulation of small molecules for the delivery of therapeutic agents, personal care products, and colorants.[2] Until recently, nearly all applications were based on nanoparticles prepared by spray drying or an oil in water emulsion approach, using homopolymers as the host. The need for "smart" particles in medical applications, to control release rates, target specific sites in the body, and to transport large biomolecules such as single strand RNA for gene therapy, instigated interest in more complicated polymer architectures and function.[3-5] A variety of architectural motifs were synthesized including many varieties of linear homopolymers and block copolymers, and branched polymers such as stars, combs, dendrimers, and hyper-branched structures that provide multiple sites (usually at chain ends) for tethering molecules. In contrast to traditional micelles, these structures are "unimolecular", and correspond to a single molecular entity formed from individual polymer chains and are unaffected by solution concentration.[6]

FIGS. 1A and 1B contrast unimolecular micelles (FIG. 1B) to traditional micelles (FIG. 1A) derived from amphiphilic block copolymers. In aqueous solutions, both assemble to form a hydrophilic (blue) exterior 2 and a hydrophobic (red) interior 1 which allows encapsulation of hydrophobic materials. Traditional polymer micelles are derived from low-cost block copolymers, but their aggregation numbers vary and block copolymers often lack functional groups for further elaboration. In addition, the critical micelle concentration (cmc) defines their lower concentration limit for in vivo applications. At low concentrations, as in the blood stream, the equilibrium between the micellar structure and individual surfactant molecules complicates controlled drug release and causes potential toxicity problems.[7] These limitations have been overcome by cross-linked micelles to form stable core shell structures,[8-17] and introducing chemical functionality to the individual molecules that of the micelle to allow introduction of moieties for cell recognition and imaging. Attaching individual hydrophobic and hydrophilic segments to a polymer backbone creates a brush-like copolymer capable of forming "unimolecular micelles." Comb polymers seem particularly promising since they can be prepared by controlled polymerization methods and the functional group density can be very high (e.g., about 1 functional group/monomer repeat unit).

There have been several recent examples of cross-linked nanoparticles synthesized by cross-linking well-defined single polymer chains. Using a dilute solution approach Hawker[18] and Harth[19] cross-linked linear styrene-vinylbenzocyclobutene copolymers and obtained ~6 nm nanoparticles. Harth extended the o-quinodimethane chemistry[19] by—copolymerizing styrene and 5-vinyl-1,3-dihydrobenzo[c]thiophene, extruding $SO_2$ to form the highly reactive o-quinodimethane intermediate and crosslink the polymer.

Thus, there exists a need for an improved drug delivery composition that can serve as a vehicle for delivering a drug in a variety of formats (e.g., encapsulated, covalently attached) in a controlled release manner.

SUMMARY

As part of ongoing interest in designing, synthesizing, and characterizing functional polylactides,[20-25] the synthesis and characterization of poly(propargyl glycolide) (poly(PGL) was recently reported.[26] Poly(PGL) is a comb polymer precursor that allows facile elaboration of the polylactide backbone via "click" chemistry: the Cu(I)-mediated 1,3-dipolar cycloaddition of azides to alkynes. Poly(PGL) "base" polymers were synthesized with molecular weights predicted by the monomer to initiator ratio, and polydispersities that ranged from 1.1-1.5. After full characterization of the base polymer, alkyl and PEO-based azides were covalently attached to the polymer backbone to obtain amphiphilic comb polymers that exhibit lower critical solution transitions over a broad temperature range. The mild conditions developed for the "click" chemistry, generating Cu(I) in situ via copper sulfate pentahydrate and sodium ascorbate in DMF at room temperature, precluded degradation of the sensitive polylactide backbone. This subject matter is disclosed in the related Baker et al. U.S. Provisional Application No. 60/966,042, which is incorporated herein by reference in its entirety.

Poly(glycolide) polymers are disclosed. The polymers generally include a glycolide-based polymer backbone that includes one or more functional groups such as alkynyl groups, hydrophilic organic triazole groups, hydrophobic organic triazole groups, di-triazole organic crosslinking groups, and triazole-substituted drug derivatives. The alkynyl groups provide reactive sites for further functionalization of the polymer, for example by reaction with azide derivatives. Alkynyl and azide groups react via the "click" chemistry mechanism to form functional groups covalently bonded to the polymer via a triazole link, for example hydrophilic organic groups, hydrophobic organic groups, crosslinking groups, and/or drug derivatives.

The polymers can be in the form of unimolecular micelles or crosslinked nanoparticles. The polymers can further encapsulate a drug for delivery to a patient (i.e., as compared to drug derivatives that are covalently attached to the polymer). Thermodynamically stable unimolecular micelles are readily prepared, and can be further crosslinked to form unimolecular crosslinked nanoparticles. The resulting compositions are completely biodegradable in both the unimolecular micelle and crosslinked nanoparticle form. The flexibility of click functionalization and crosslinking allows the design of compositions applicable to a wide variety of controlled-release drug delivery applications.

In a first embodiment, a poly(glycolide) polymer comprises: one or more repeating units according to Formula I

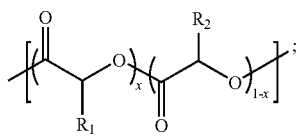

[Formula I]

wherein: (i) $R_1$ comprises one or more moieties selected from an alkynyl group, a hydrophilic organic triazole group, a hydrophobic organic triazole group, a triazole organic crosslinking group (e.g., di-triazole organic crosslinking group), a triazole-substituted liquid crystal mesogen, a triazole-substituted dye, and a triazole-substituted drug derivative; (ii) $R_2$ comprises one or more moieties selected from a hydrogen, an alkyl group, an alkynyl group, a hydrophilic organic triazole group, a hydrophobic organic triazole group, a triazole organic crosslinking group (e.g., di-triazole organic crosslinking group), a triazole-substituted liquid crystal mesogen, a triazole-substituted dye, and a triazole-substituted drug derivative; and, (iii) x is between 0 and 1.

In variations of the first embodiment, the alkynyl group comprises 3 to 12 carbon atoms (e.g., a propargyl group having a terminal alkynyl group), the alkyl group comprises 1 to 18 carbon atoms, the hydrophilic organic triazole group comprises a triazole reaction product of an alkynyl group and an azide-substituted polyoxyethylene (e.g., the triazole reaction product of a propargyl group and azidoethyl tetraethylene glycol methyl ether), the hydrophobic organic triazole group comprises a triazole reaction product of an alkynyl group and an azide-substituted alkane (e.g., the triazole reaction product of a propargyl group and 1-azidodecane), the triazole organic crosslinking group comprises a di-triazole reaction product of two alkynyl groups and a diazido alkane (e.g., the di-triazole reaction product of two propargyl groups and a 1,5-diazidopentane), and/or the triazole-substituted drug derivative comprises a triazole reaction product of an alkynyl group and an azide-substituted drug. Alternatively, the hydrophilic organic triazole group comprises a triazole reaction product of an alkynyl group and a moiety selected from the group consisting of an azide-substituted polyoxyethylene polyoxyalkylene, an azide-substituted organic amine, an azide-substituted carboxylic acid, an azide-substituted carboxylate salt, an azide-substituted alkyl polyoxyalkylene, an azide-substituted ketone, an azide-substituted alcohol, an azide-substituted ester, and combinations thereof (e.g., the hydrophilic organic triazole group can include a distribution of multiple types of groups, with a single group attached at each $R_1$ or $R_2$ location). Preferably, $R_1$ is the hydrophilic organic triazole group and x ranges from 0.5 to 0.95, and $R_2$ comprises the di-triazole organic crosslinking group (and optionally the triazole-substituted drug derivative in addition). The poly(glycolide) polymer can be in the form of a copolymer (e.g., random or block) that further comprises lactide repeating units.

In a second embodiment, a poly(glycolide) polymer comprises: one or more polymeric chains according to Formula II

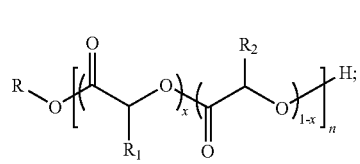

[Formula II]

wherein: (i) $R_1$ comprises one or more moieties selected from an alkynyl group and a triazole organic crosslinking group (e.g., di-triazole organic crosslinking group); (ii) $R_2$ comprises a hydrophilic organic triazole group and optionally one or more moieties selected from a hydrogen, an alkyl group, an alkynyl group, a hydrophobic organic triazole group, a triazole-substituted liquid crystal mesogen, a triazole-substituted dye, and a triazole-substituted drug derivative; (iii) R comprises a terminal group (e.g., a hydrogen or an alkyl group); (iv) x ranges from 0 to less than 1; and, (v) n ranges from about 10 to about 1000.

In variations of the second embodiment, the alkynyl group comprises 3 to 12 carbon atoms (e.g., a propargyl group having a terminal alkynyl group), the alkyl group comprises 1 to 18 carbon atoms, the hydrophilic organic triazole group comprises a triazole reaction product of an alkynyl group and an azide-substituted polyoxyethylene and/or any of the above azide-substituted hydrophilic groups (e.g., the triazole reaction product of a propargyl group and azidoethyl tetraethylene glycol methyl ether), the hydrophobic organic triazole group comprises a triazole reaction product of an alkynyl group and an azide-substituted alkane (e.g., the triazole reaction product of a propargyl group and 1-azidodecane), the triazole organic crosslinking group comprises a di-triazole reaction product of two alkynyl groups and a diazido alkane (e.g., the di-triazole reaction product of two propargyl groups and a 1,5-diazidopentane), and/or the triazole-substituted drug derivative comprises a triazole reaction product of an alkynyl group and an azide-substituted drug. The polymer can be in the form of a unimolecular micelle having a diameter of about 50 nm or less (e.g., about 15 nm to about 50 nm; as measured by dynamic light scattering in aqueous solution) with a substantially hydrophilic exterior and a substantially hydrophobic interior. The polymer also can be in the form of an intramolecularly crosslinked nanoparticle having a diameter of about 35 nm or less (e.g., about 8 nm to about 35 nm; as measured by dynamic light scattering in aqueous solution) with a substantially hydrophilic exterior and a substantially hydrophobic interior when $R_1$ comprises the di-triazole organic crosslinking group and x is larger than 0. The polymer also can comprise a plurality of crosslinked nanoparticles having a distribution of crosslinking degrees selected to control the rate of release of an encapsulated component or a covalently bound component in the plurality of crosslinked nanoparticles. Either the unimolecular micelle or the crosslinked nanoparticle can further comprise an encapsulated drug within the interior, or a covalently bound triazole-substituted drug derivative.

In a third embodiment, a poly(glycolide) polymer comprises: a triazole reaction product of (a) an alkynyl glycolide according to Formula III

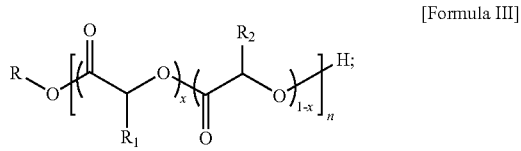

[Formula III]

(b) an azide-substituted hydrophilic organic compound; and, (c) optionally one or more of a azido organic crosslinker (e.g., a diazido organic crosslinker), an azide-substituted hydrophobic organic compound, an azide-substituted liquid crystal mesogen, an azide-substituted dye, and an azide-substituted drug; wherein: (i) $R_1$ comprises one or more moieties selected from a hydrogen, an alkyl group, and an alkynyl group; (ii) $R_2$ comprises an alkynyl group; (iii) R comprises a terminal group (e.g., a hydrogen or an alkyl group); (iv) x ranges from 0 to less than 1; and, (v) n ranges from about 10 to about 1000.

In variations of the third embodiment, the alkynyl group comprises 3 to 12 carbon atoms (e.g., a propargyl group having a terminal alkynyl group), the alkyl group comprises 1 to 18 carbon atoms, and/or the azide-substituted hydrophilic organic compound comprises an azide-substituted polyoxyethylene (e.g., azidoethyl tetraethylene glycol methyl ether or any of the above general azide-substituted hydrophilic organic compounds). The polymer can be in the form of a unimolecular micelle having a diameter of about 50 nm or less (e.g., about 15 nm to about 50 nm; as measured by dynamic light scattering in aqueous solution) with a substantially hydrophilic exterior and a substantially hydrophobic interior. The polymer also can be in the form of an intramolecularly crosslinked nanoparticle having a diameter of about 35 nm or less (e.g., about 8 nm to about 35 nm; as measured by dynamic light scattering in aqueous solution) with a substantially hydrophilic exterior and a substantially hydrophobic interior when the triazole reaction product comprises moieties resulting from the reaction of the alkynyl glycolide according to Formula III and the azido organic crosslinker. The polymer also can comprise a plurality of crosslinked nanoparticles having a distribution of crosslinking degrees selected to control the rate of release of an encapsulated component or a covalently bound component in the plurality of crosslinked nanoparticles. Either the unimolecular micelle or the crosslinked nanoparticle can further comprise an encapsulated drug within the interior, or a covalently bound triazole-substituted drug derivative.

Also disclosed is a method of delivering a drug-compound to a cell, the method comprising: (a) providing the drug compound with the poly(glycolide) polymer of any of the foregoing embodiments; and, (b) releasing the drug compound to the cell over a period of time. The cell can be in vivo or in vitro, and the poly(glycolide) polymer can be in the form of a unimolecular micelle or an intramolecularly crosslinked nanoparticle. In an embodiment, the drug compound comprises a triazole-substituted drug derivative covalently bound to the poly(glycolide) polymer. In another embodiment, the drug compound is encapsulated by the poly(glycolide) polymer. In yet another embodiment, the drug compound is in dosage unit form with a carrier.

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein:

FIG. 5b illustrates the fluorescence intensity of crosslinked nanoparticles having an azide-substituted fluorescent dye precursor bound to the crosslinked nanoparticle according to the different reaction paths of FIG. 5a.

Figure 1A:
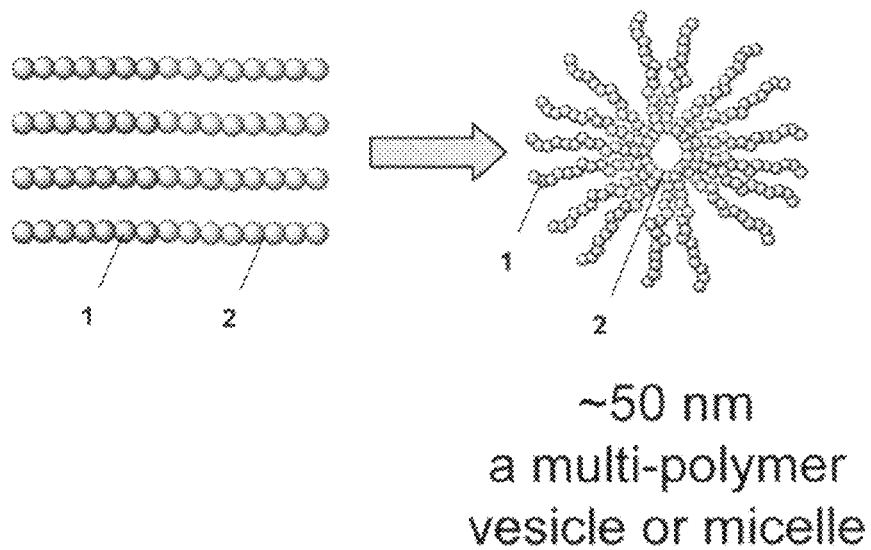
FIGS. 1a and 1b are schematics comparing a traditional micelle formed from block copolymers (FIG. 1a) and the formation of a unimolecular micelle (FIG. 1b) from an amphiphilic comb polymer in aqueous solution. The hydrophilic (blue; 1) chains are soluble in the aqueous phase, while hydrophobic segments (red; 2) collapse into the interior of the micelle.
Figure 1B:
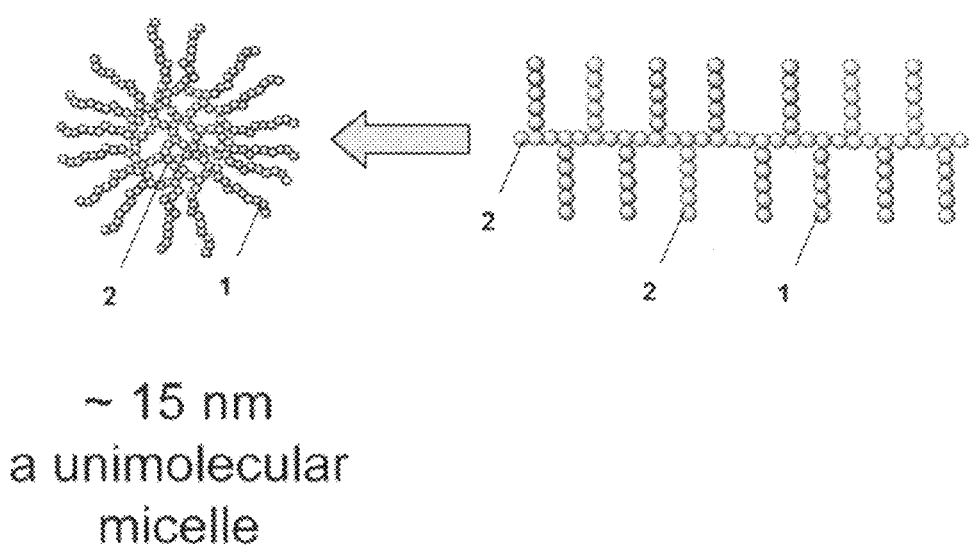

While the disclosed compositions and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

Poly(glycolide) polymers are disclosed. The polymers generally include a glycolide-based polymer backbone that includes one or more functional groups such as alkynyl groups, hydrophilic organic triazole groups, hydrophobic organic triazole groups (also including amphiphilic organic triazole groups), di-triazole organic crosslinking groups, and triazole-substituted drug derivatives. The alkynyl groups provide reactive sites for further functionalization of the polymer, for example by reaction with azide derivatives. Alkynyl and azide groups react via the "click" chemistry mechanism to form functional groups covalently bonded to the polymer via a triazole link, for example hydrophilic organic groups, hydrophobic organic groups, crosslinking groups, and/or drug derivatives. The polymers can be in the form of unimolecular micelles or crosslinked nanoparticles. The polymers can further encapsulate a drug for delivery to a patient (i.e., as compared to drug derivatives that are covalently attached to the polymer).

As used herein, the term "glycolide" refers to the reaction product when two mono-basic hydroxy acids form a cyclic diester containing four (4) carbon atoms and two (2) oxygen atoms in the ring. The basic ring structure is a dioxandione (i.e., the condensation product of two glycolic acid (2-hydroxyethanoic acid) molecules). The glycolide monomer according to the disclosure has an alkynyl group substituted on at least one (e.g., on one or two) of the carbon atoms in the ring structure. A poly(glycolide) polymer (or polyglycolide) includes a polymer resulting from the ring-opening polymerization of the alkynyl-substituted glycolide monomer. The alkynyl-substituted glycolide for producing heteropolymers can have various substituents (e.g., aliphatic (alkyl, alkenyl, etc.), aromatic (aryl, etc.)) on the carbon atoms along with the alkynyl groups. A "lactide" is a type of glycolide and refers to the cyclic diester condensation product of two 3-carbon α-hydroxy acids, particularly when the α-hydroxy acid is lactic acid (2-hydroxypropanoic acid). A poly(lactide) polymer (or polylactide) includes a polymer of a lactide.

Poly(Glycolide) Polymers

The poly(glycolide) polymers according to the disclosure can generally be described in various forms: (1) in terms of repeating units contained in the polymer, (2) in terms of the polymeric chain itself, and/or (3) as the reaction product of its precursors.

In a first embodiment, the poly(glycolide) polymer includes one or more repeating units according to Formula I:

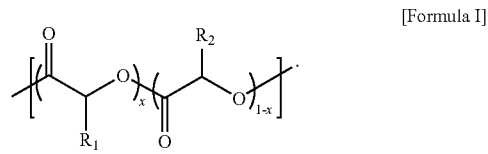

[Formula I]

In Formula I: (i) $R_1$ includes one or more of an alkynyl group, a hydrophilic organic triazole group, a hydrophobic organic triazole group, a triazole organic crosslinking group, a triazole-substituted liquid crystal mesogen, a triazole-substituted dye, and a triazole-substituted drug derivative; and (ii) $R_2$ includes one or more of a hydrogen, an alkyl group, an alkynyl group, a hydrophilic organic triazole group, a hydrophobic organic triazole group, a triazole organic crosslinking group, a triazole-substituted liquid crystal mesogen, a triazole-substituted dye, and a triazole-substituted drug derivative. When x is 0 and $R_2$ is uniformly hydrogen, Formula I simply represents an unmodified poly(glycolide). The polymers according to the disclosure, however, contain at least some degree of functionalization; accordingly, x is greater than zero (e.g., x is between 0 and 1).

In a second embodiment, the poly(glycolide) polymer includes one or more polymeric chains according to Formula II:

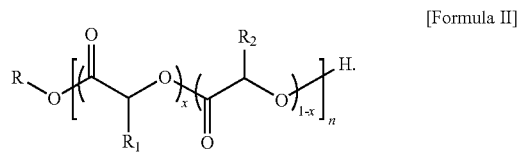

[Formula II]

In Formula II: (i) $R_1$ includes one or more of a hydrogen, an alkyl group, an alkynyl group, and a triazole organic crosslinking group; (ii) $R_2$ includes a hydrophilic organic triazole group and optionally one or more of a hydrogen, an alkyl group, an alkynyl group, a hydrophobic organic triazole group, a triazole-substituted liquid crystal mesogen, a triazole-substituted dye, and a triazole-substituted drug derivative; and (iii) R includes a terminal group (e.g., a hydrogen, an alkyl group, for example a $C_1$-$C_{10}$ alkyl group). In this embodiment, x ranges from 0 to less than 1, thereby requiring at least some of the hydrophilic organic triazole group via the $R_2$ moiety. A wide variety of degrees of polymerization are acceptable, and n suitably ranges from about 10 to about 1000 (preferably about 20 to about 400, or about 20 to about 200).

In a third embodiment, the poly(glycolide) polymer includes a triazole reaction product of (a) an alkynyl glycolide according to Formula III

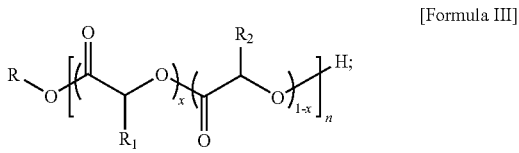

[Formula III]

(b) an azide-substituted hydrophilic organic compound; and, (c) optionally one or more of an azido organic crosslinker, an azide-substituted hydrophobic organic compound, an azide-substituted liquid crystal mesogen, an azide-substituted dye, and an azide-substituted drug. In Formula III: (i) $R_1$ includes one or more of a hydrogen, an alkyl group, and an alkynyl group; (ii) $R_2$ includes an alkynyl group; and (iii) R includes a terminal group (e.g., a hydrogen, an alkyl group, for example a $C_1$-$C_{10}$ alkyl group). Similar to the previous embodiment, x ranges from 0 to less than 1, and n ranges from about 10 to about 1000 (preferably about 20 to about 400, or about 20 to about 200).

The groups $R_1$ and $R_2$ in the forgoing structures can generally include alkynyl groups. Such groups are generally hydrocarbons having at least one (e.g., only one) alkynyl functionality (—C≡C—, for example —C≡CH) that serves as a reactive site for the 1,3-dipolar cycloaddition of a functionalized azide to the polymer backbone, resulting in a triazole group linking the azide-functional group to the polymer backbone (described below). The alkynyl groups preferably have 2 to 20 carbons, for example 3 to 12 carbons or 3 to 6 carbons. Preferably, the alkynyl groups are linear and the alkynyl functionality is located at the terminal position in the hydrocarbon chain (i.e., at the furthest position away from the polymer backbone). For example, a suitable alkynyl group includes the 1-propynyl (or propargyl) group bonded to the polymer backbone at the 3-carbon position (e.g., as illustrated in structure 4 of FIG. 2).

Functionalized Poly(Glycolide) Polymers

The poly(glycolide) polymer can be functionalized to impart desired features to the basic polymer. The functionalized poly(glycolide) polymer generally includes the triazole reaction product of the poly(glycolide) polymer and an azide-substituted organic compound (at least one of which preferably is a hydrophilic azide-substituted organic compound). In this case, the groups $R_1$ and $R_2$ in the foregoing structures can additionally represent the triazole reaction product of the $R_1$ and $R_2$ alkynyl groups in the original poly(glycolide) polymer and the azide-substituted organic compound, for example as illustrated in structure 6 of FIG. 2 for the case where the azide-substituted organic compounds are di-azide-substituted alkanes (i.e., crosslinkers) and azide-substituted polyoxyethylenes.

Figure 10:
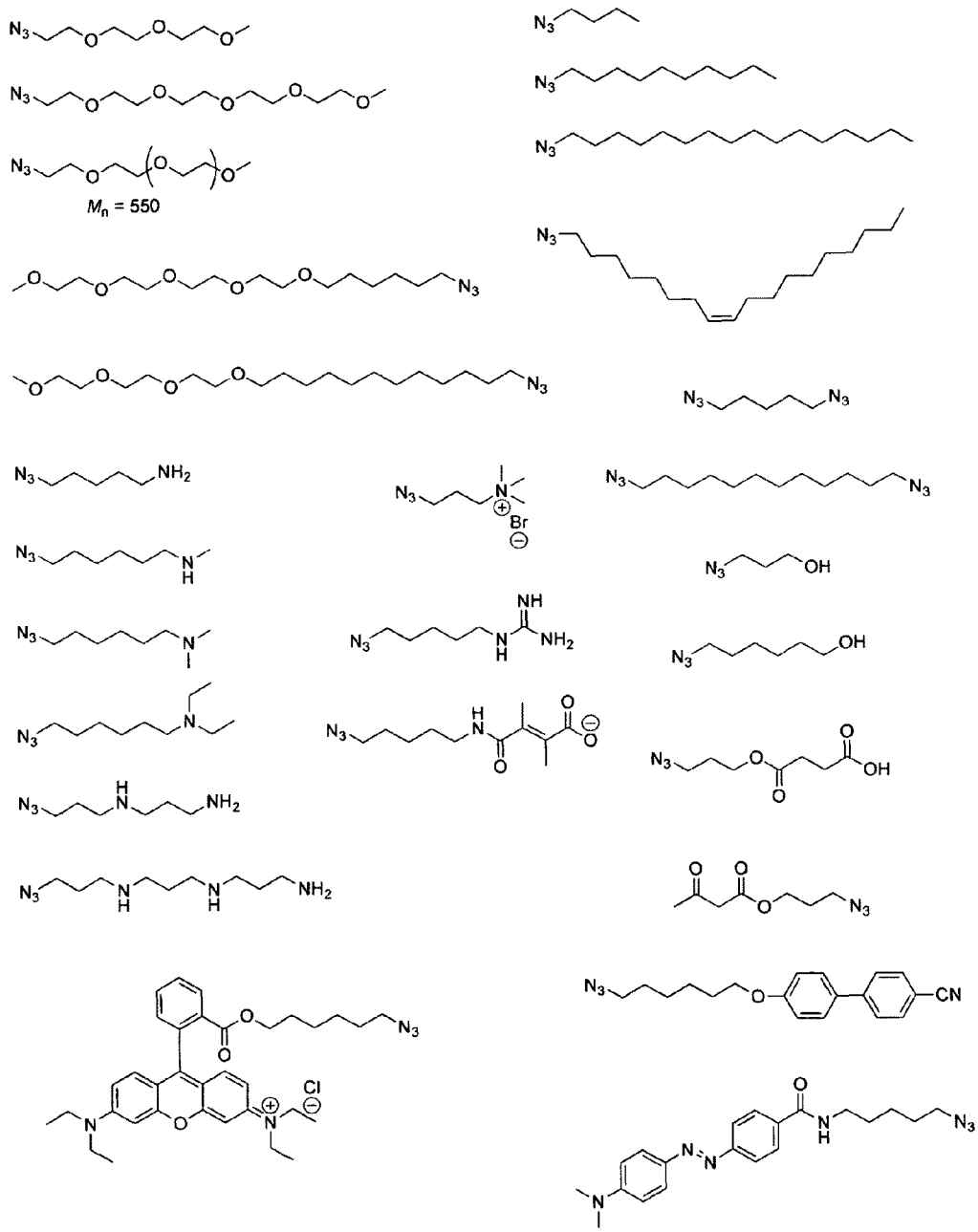
FIG. 10 illustrates representative chemical structures of azide-substituted organic compounds capable of click-functionalization on the poly(glycolide) polymer.

The azide-substituted organic compounds are not particularly limited, generally including hydrophilic organic azido groups, hydrophobic organic azido groups (also including amphiphilic organic azido groups), azido organic crosslinking groups (e.g., diazido crosslinking groups), azide-substituted drug derivatives, azide-substituted dye derivatives, and azide-substituted liquid crystal mesogens, for example including the variety of representative structures illustrated in FIG. 10. Examples of suitable azide-substituted organic compounds include azide-substituted polyoxyalkylenes, azide-substituted organic amines (and ammonium salts thereof), azide-substituted organic amides, azide-substituted organic imines, an azide-substituted carboxylic acid, azide-substituted carbonyl-containing compounds (e.g., ketones, carboxylic acids, carboxylate salts, esters), azide-substituted alkyl polyoxyalkylenes, azide-substituted alcohols, azide-substituted alkanes, azide-substituted alkenes, diazido alkanes, and azide-substituted dyes. FIG. 10 illustrates (bottom left structure) a derivative of a rhodamine B dye having an alkyl azide tether that hydrolyzes in an aqueous environment to release the dye. FIG. 10 further illustrates (bottom two structures on right) representative liquid crystal mesogens (i.e., azide-substituted molecules exhibiting liquid crystal behavior and having both a rigid aryl/aromatic portion and a flexible aliphatic/alkyl portion to which the azido group can be attached). In some embodiments, the azide-substituted organic compound can include more than one of the foregoing functional groups, for example as illustrated in FIG. 10 (e.g., the 3-azidopropyl ester of butanedioic acid illustrated containing both ester and carboxylic acids functionalities).

Hydrophilic Organic Triazole Groups: The groups $R_1$ and $R_2$ in the forgoing structures can generally include hydrophilic organic triazole groups. The hydrophilic organic triazole groups promote the compatibility of the functionalized poly(glycolide) polymer with water and facilitate the formation of a stable, unimolecular micelle in an aqueous environment. The hydrophilic organic triazole groups preferably include reaction products (e.g., click reaction products) of a polymer backbone-pendant alkynyl groups (above) and an azide-substituted polyoxyethylene. For example, suitable azide-substituted polyoxyethylenes can generally be polyethylene glycols of the form $N_3[C_2H_4O]_nR$, where n preferably ranges from 2 to 20 (e.g., 3 to 15 or 3 to 8) and R is a terminal group (e.g., a hydrogen, an alkyl group, for example a $C_1$-$C_{10}$ alkyl group). Equivalently, the resulting hydrophilic organic triazole group can be represented by -Tr[$C_2H_4O]_nR$, where n and R are as before, and Tr is a 1,4-disubstituted 1,2,3-triazole (i.e., linked to the polyoxyethylene at the 1-position of the triazole and linked to the polymer backbone via the 4-position of the triazole). A preferred azide-substituted polyoxyethylene is azidoethyl tetraethylene glycol methyl ether (i.e., n is 5 and R is methyl in the foregoing generic azide derivative), and the resulting hydrophilic organic triazole is illustrated in structure 5 of FIG. 2 (top pendant group; for the case when the alkynyl group is the propargyl group). Other suitable azide-substituted polyoxyethylenes include PEG-550 monomethyl ether ("mPEG") and 10-axido-2,5,8-trioxadecane ("mDEG", where n is 3 and R is methyl in the foregoing generic azide derivative). The azide-substituted polyoxyethylene can be formed by methods generally known in the art, for example by tosylating a polyoxyethylene (e.g., PEG-550 monomethyl ether or the aforementioned pentaethylene glycol methyl ether) and reacting the same with an azide salt (e.g., sodium azide).

As used herein, the term "hydrophilic" as applied to organic triazole groups can include organic triazole groups (or their organic azide precursors) that contain substantially exclusively hydrophilic units. Examples of suitable hydrophilic units include alkoxy groups (e.g., methoxy, ethoxy (preferable), propoxy, higher alkoxy), organic amino groups (e.g., primary, secondary, tertiary), carbonyl groups (e.g., ketones), carboxylic groups (e.g., in acid and/or salt form, including alkali metal salts), hydroxyl groups, and esters. The term "hydrophilic" additionally can include amphiphilic organic triazole groups (and precursors) that contain both hydrophilic units and hydrophobic units; however, the amphiphilic organic triazole groups have sufficient hydrophilic character to form a stable, unimolecular micelle in an aqueous environment. Thus, the above example azide-substituted polyoxyethylene of the form $N_3[C_2H_4O]_nR$ would generally be characterized as substantially exclusively hydrophilic when R is a hydrogen or a methyl group, based on the hydrophilic nature of the ethoxy —$C_2H_4O$— unit; as the number of carbons in R increases, however, the azide-substituted polyoxyethylene assumes more hydrophobic character, but would still be sufficiently hydrophilic (i.e., amphiphilic) to form unimolecular micelles in an aqueous environment.

The azide-substituted hydrophilic organic groups generally have an aliphatic hydrocarbon base structure (e.g., linear alkyl) with the hydrophilic unit(s) located at one or more positions along the length of the hydrocarbon base structure. The hydrocarbon base structure can be of variable size depending of the desired properties of the functionalized polymer; common sizes generally range from 1 to 50 carbon atoms, for example from 2 to 30 carbon atoms, 2 to 20 carbon atoms, or 3 to 12 carbon atoms. Examples of suitable hydrophilic (or amphiphilic) azide-substituted triazole precursors include azide-substituted polyoxyalkylenes (e.g., 4 to 50 carbon atoms or 6 to 20 carbon atoms, including the polyoxyethylenes described above), azide-substituted organic amines and ammonium salts thereof (e.g., 1 to 20 carbon atoms (or 2 to 10 carbon atoms) and having at least one amino/ammonium group), azide-substituted carboxylic acids/salts thereof (e.g., 1 to 20 carbon atoms (or 2 to 10 carbon atoms) and having at least one (preferably terminal) carboxylic group), and azide-substituted alcohols, ketones, ethers, esters, imines, and amides (e.g., 1 to 20 carbon atoms or 2 to 10 carbon atoms). Other, generally amphiphilic suitable azide-substituted triazole precursors can include azide-substituted alkyl groups (e.g., 1 to 20 carbon atoms or 2 to 10 carbon atoms) terminated with polyoxyalkylenes (e.g., 4 to 50 carbon atoms or 6 to 20 carbon atoms). For example, such an amphiphilic triazole precursor can be of the form $N_3R_a[C_2H_4O]_nR$, where n and R are as before, and $R_a$ is an alkyl group (e.g., a $C_1$-$C_{20}$ alkyl group or a $C_2$-$C_{10}$ alkyl group).

Hydrophobic Organic Triazole Groups: The groups $R_1$ and $R_2$ in the forgoing structures can include hydrophobic organic triazole groups in some embodiments (e.g., resulting from the click functionalization of azide-substituted hydrophobic organic groups). The hydrophobic organic triazole groups can be included in the polymer, for example, to adjust the molecular weight of the polymer, to adjust the hydrophilic/hydrophobic balance in the final polymer, and/or to obtain lower critical solution temperature (LCST) behavior. The hydrophobic organic triazole groups also can be included in the polymer to an extent sufficient to induce the formation of inverse micelles in a non-aqueous solution (i.e., a substantially hydrophobic exterior that promotes compatibility with a non-aqueous solvent and a substantially hydrophilic interior that promotes, for example, compatibility with an encapsulated hydrophilic drug or other compound). The azide-substituted hydrophobic organic groups generally have an aliphatic hydrocarbon, for example including linear or branched alkyl or alkenyl hydrocarbons. The hydrophobic aliphatic hydrocarbon can be of variable size depending on the desired properties of the functionalized polymer; common sizes generally range from 1 to 50 carbon atoms, for example from 2 to 30 carbon atoms, 2 to 20 carbon atoms, or 3 to 12 carbon atoms. The hydrophobic organic triazole groups preferably include reaction products of polymer backbone-pendant alkynyl groups and azide-substituted alkanes. For example, suitable azide-substituted alkanes can generally be of the form $N_3[CH_2]_nCH_3$, where n preferably ranges from 2 to 20, for example from 4 to 16 or 6 to 14. Equivalently, the resulting hydrophobic organic triazole group can be represented by -Tr$[CH_2]_nCH_3$, where n is as before, and Tr is a 1,4-disubstituted 1,2,3-triazole (i.e., linked to the alkane at the 1-position of the triazole and linked to the polymer backbone via the 4-position of the triazole). Preferred azide-substituted alkanes are 1-azidobutane, 1-azidodecane, and 1-azidohexadecane (i.e., n is 3, 9, and 15, respectively; illustrated in FIG. 10). The hydrophobic organic triazole groups can similarly include reaction products of polymer backbone-pendant alkynyl groups and azide-substituted alkenes. The azide-substituted alkenes are similarly sized to the alkanes, for example including 1-azidooctadec-8-ene (illustrated in FIG. 10). The azide-substituted alkane/alkene can be formed by methods generally known in the art, for example by reacting a halogenated alkane/alkene with an azide salt (e.g., 1-bromodecane with sodium azide).

Non-Triazole Groups: The groups $R_1$ and $R_2$ in the forgoing structures, when not representing an alkynyl group or a triazole derivative thereof, can include hydrogen or other organic groups. The organic group is not particularly limited, generally including aliphatic hydrocarbon groups (linear or branched, including alkyl or alkenyl) and/or aromatic (aryl) hydrocarbon groups. The alkyl groups (and the other non-triazole organic groups in general) provide a similar functionality to the hydrophobic organic triazole groups above (e.g., adjust the molecular weight, adjust the hydrophilic/hydrophobic balance, induce the formation of inverse micelles). The organic groups differ structurally, however, in that they are appended directly to the polymer backbone, absent a triazole linkage. In this embodiment, the organic group is preferably integrated into the polymer by appending the organic group to a glycolide monomer. For example, a di-alkyl-substituted glycolide (e.g., lactide, where the alkyl group is —$CH_3$) can be copolymerized with a di-alkynyl-substituted glycolide (e.g., structure 3 of FIG. 2). Alternatively or additionally, an alkyl-substituted derivative of glycolic acid (e.g., lactic acid, where the alkyl group is —$CH_3$) can be condensed with an alkynyl-substituted derivative of glycolic acid (e.g., structure 2 of FIG. 2), thereby forming a blend of a di-alkyl-substituted glycolide (e.g., lactide), a di-alkynyl-substituted glycolide (e.g., structure 3 of FIG. 2), and an alkyl-alkynyl-substituted glycolide (e.g., 3-(2-propynyl)-6-methyl-1,4-dioxane-2,5-dione). The resulting blend of glycolide derivatives can then be copolymerized to form a polymer having a desired distribution of alkyl and alkynyl functionalities. The organic group can have from 0 to 20 carbon atoms (where "0" represents a limiting case in which the alkyl group is a hydrogen atom), for example 1 to 18 carbon atoms, 1 to 12 carbon atoms, or 1 to 6 carbon atoms.

Figure 2:
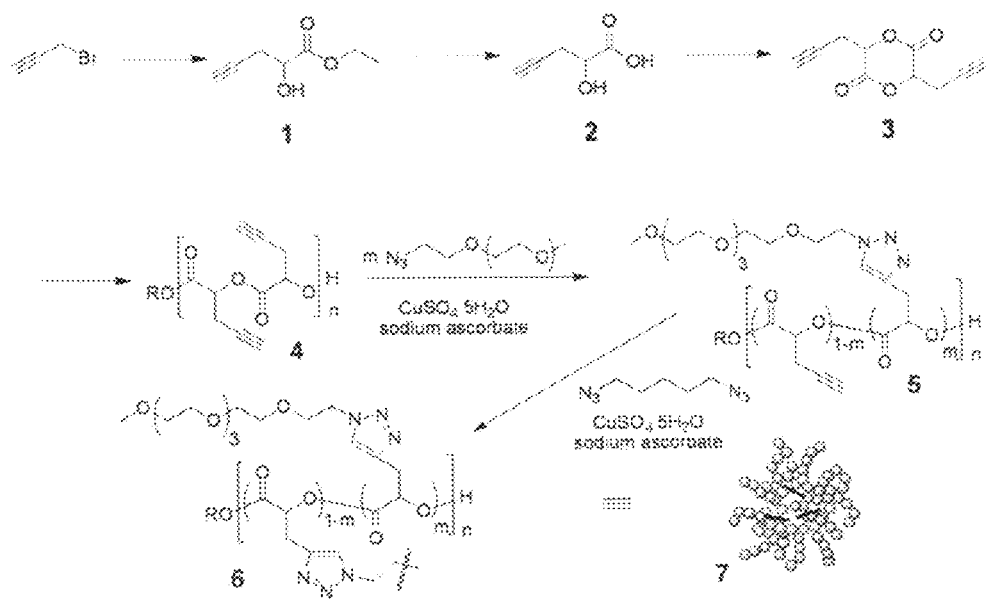
FIG. 2 illustrates the synthesis and crosslinking of unimolecular micelles from propargyl glycolide, azidoethyl tetraethylene glycol methyl ether, and 1,5-diazidopentane.
Figure 2:
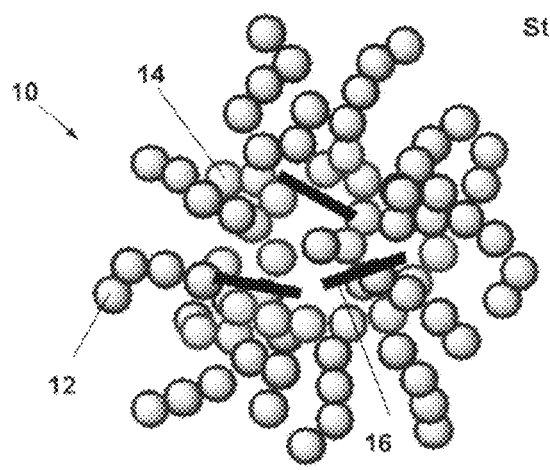

Crosslinking Groups: In some embodiments, the poly(glycolide) polymer can be crosslinked. The crosslinking can be inter- and/or intramolecular in nature. Crosslinked nanoparticles include intramolecular crosslinks that link neighboring portions of the polymer backbone when the polymer is in a micellar configuration, thereby forming the nanoparticle. Crosslinking is generally effected by reacting a diazido organic crosslinking compound with two free alkynyl groups on the polymer backbone, thereby forming a di-triazole organic crosslinking group between the two polymer backbone locations. Suitable diazido organic crosslinking compounds include diazido alkanes, for example $N_3[CH_2]_nN_3$, where n preferably ranges from 1 to 20, for example from 2 to 10 or 3 to 8. A preferred diazido alkane is 1,5-diazidopentane, and the resulting crosslinked structure is illustrated in structure 6 of FIG. 2 (bottom pendant group; for the case when the alkynyl group is the propargyl group). Other suitable diazido alkanes include 1,12-diazidododecane (FIG. 10). Other multi-functional azido organic crosslinking compounds can be used, for example including triazido functional (or higher) crosslinking compounds such as triazido (or higher) alkanes (preferably branched). FIG. 2 (structure 7) and FIG. 4a further qualitatively illustrate the crosslinking process and structure. Specifically, structure 7 in FIG. 2 has a crosslinked nanoparticle 10 having hydrophilic organic triazole groups 12 that outwardly project from a poly(glycolide) polymer backbone 14 forming the interior of the crosslinked nanoparticle 10. The crosslinks 16 represent the di-triazole organic crosslinking groups between different regions of the polymer backbone 14. The diazido alkanes can be formed, for example, reacting a di-halogenated alkane with an azide salt (e.g., 1,5-dibromopentane with sodium azide).

Drug Delivery: The poly(glycolide) polymer can be used as a vehicle for the controlled release of a drug. In some embodiments, the any of a variety of biologically relevant drugs can be covalently attached to the polymer, for example when the polymer is in the form of a polymeric chain, a unimolecular micelle, or a crosslinked nanoparticle. A particular drug of interest is functionalized using conventional methods so that the drug molecule is azide-substituted (e.g., halogenation or tosylation of an alkyl group followed by reaction with an azide salt, synthesis of aromatic azides from the corresponding amines by reaction with t-butyl nitrite and azidotrimethylsilane, ring-opening of epoxides to form 1,2-azido alcohols, etc.). The drug is then attached to the polymer as the triazole reaction product of the azide-substituted drug and a free pendant alkynyl group along the polymer backbone. In general, any drug that can be modified to include a pendant azide without destroying (or otherwise substantially inhibiting) the activity of the drug can be used. Preferably, an azide tether (i.e., an azide group with an optional linking group between the azide group and the drug) is used that is able to hydrolyze to reveal the drug. For example, an azide tether can include an alkyl (or other hydrocarbon) group having an ester linkage to the drug at one end of the alkyl group and an azide group at the opposing end of the alkyl group, thus allowing ester hydrolysis to release the drug in an aqueous environment (e.g., as illustrated by the drug surrogate rhodamine B azide derivative in FIG. 10).

Poly(glycolide) Copoloymers: In some embodiments, the poly(glycolide) polymer can be a copolymer, for example a copolymer incorporating other biodegradable repeating units. The inclusion of a comonomer can be used to alter the density of functional groups (i.e., alkynyl groups and/or triazole derivatives thereof) along the polymer backbone while retaining the biodegradable character of the polymer as a whole. A preferred copolymer includes a poly(glycolide-lactide) copolymer that further includes lactide repeating units with glycolide repeating units along the polymer backbone (e.g., as described above for embodiments in which $R_1$ and/or $R_2$ include alkyl groups). Other suitable copolymer repeating units include polyester units having from 2 to 10 carbon atoms in the repeating unit along the length of the polymer backbone (e.g., including the repeating unit derived from copolymerization with ε-caprolactone). In such a case, the copolymer can be a block copolymer (e.g., when the poly (glycolide) polymer is further reacted with a lactide monomer) or a random copolymer (e.g., when a glycolide monomer such as propargyl glycolide is reacted with a lactide or other monomer).

Polymer Characteristics: In the foregoing embodiments, the poly(glycolide) polymer generally includes a variety of groups along its backbone, for example hydrogens, alkynyl groups, hydrophilic organic triazole groups, hydrophobic organic triazole groups (also including amphiphilic organic triazole groups), di-triazole organic crosslinking groups, and triazole-substituted drug derivatives. The various groups can be included in the polymer in various proportions according to desired properties of the final polymer. The polymer backbone requires at least some alkynyl groups to facilitate subsequent polymer functionalization via triazole formation. Thus, while some of the backbone groups can include non-functional hydrogens, the alkynyl glycolide precursor (e.g., as represented by Formula III) preferably is saturated with alkynyl groups (i.e., all or substantially all of the $R_1$ and $R_2$ in Formula III are alkynyl groups).

In a preferred embodiment, the poly(glycolide) polymer includes a substantial fraction of hydrophilic organic triazole groups at its functional positions $R_1$ and $R_2$. For example, preferably about 50% to about 95% of the functional positions $R_1$ and $R_2$ available in the polymer are occupied by one or more types of hydrophilic organic triazole groups, more preferably about 60% to about 90% (or about 65% to about 85%), for example about 75%. Within the context of Formula I, for example, this corresponds to a structure in which (i) $R_1$ represents hydrophilic organic triazole groups and x ranges from about 0.5 to about 0.95 (or about 0.6 to about 0.9, about 0.65 to about 0.85, or about 0.75), and (ii) $R_2$ represents non-hydrophilic organic triazole groups (e.g., unreacted alkynyl groups, di-triazole organic crosslinking groups, triazole-substituted drug derivatives). In a further embodiment, the remaining functional positions $R_1$ and $R_2$ (i.e., those that include alkynyl groups not converted to hydrophilic organic triazole groups) can be crosslinked and/or used as sites for covalent drug attachment. For example, about 10% to about 100% of the available alkynyl groups remaining after functionalization with the hydrophilic organic triazole groups can be crosslinked with di-triazole organic crosslinking groups. Alternatively, about 5% to about 50% of the functional positions $R_1$ and $R_2$ available in the polymer are occupied by di-triazole organic crosslinking groups, more preferably about 10% to about 40%, or about 15% to about 35%. When the final poly(glycolide) polymer is to include a triazole-substituted drug derivative, the polymer is not saturated with the diazido organic crosslinker to preserve some alkynyl groups for drug attachment.

In another embodiment, the poly(glycolide) polymer includes a lower fraction of hydrophilic organic triazole groups at its functional positions $R_1$ and $R_2$ to permit a higher degree of incorporation of non-hydrophilic functional groups (e.g., hydrophobic groups (whether attached directly to the polymer backbone or via a triazole linkage), liquid crystal mesogens attached via a triazole linkage). For example, about 10% to about 50% of the functional positions $R_1$ and $R_2$ available in the polymer can be occupied by hydrophilic organic triazole groups, for example about 15% to about 45% (or about 20% to about 40%). Similarly, about 10% to about 50% of the functional positions $R_1$ and $R_2$ available in the polymer can be occupied by non-hydrophilic functional groups, for example about 15% to about 45% (or about 20% to about 40%). In any event, a portion of the functional positions $R_1$ and $R_2$ still can be utilized for crosslinking and/or drug attachment, for example at levels similar to the foregoing embodiment containing a substantial fraction of hydrophilic organic triazole groups.

Unimolecular Polymer Configurations

Figure 5A:
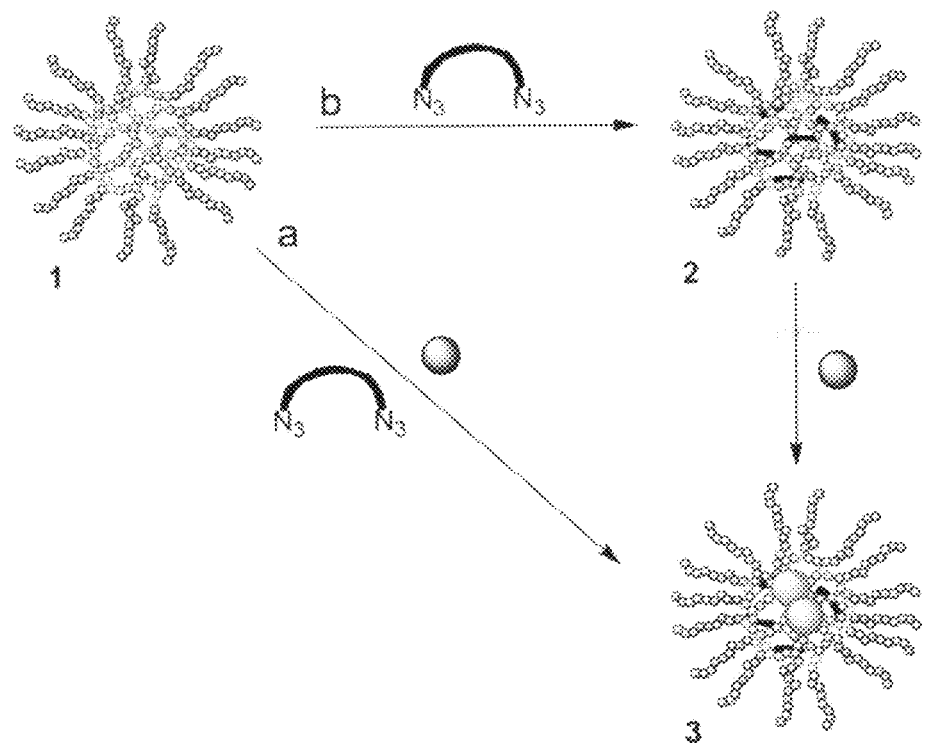
FIG. 5a is a schematic illustrating two different reaction paths for the covalent binding of an azide-substituted drug to a crosslinked nanoparticle.

The poly(glycolide) polymer can assume a unimolecular micellar configuration in an aqueous solution when the polymer includes pendant hydrophilic organic triazole groups. The unimolecular micelle self-aggregates and configurationally rearranges in the aqueous solution such that the micelle has a substantially hydrophilic exterior (e.g., resulting from the outwardly protruding hydrophilic organic triazole groups on the polymer backbone) and a substantially hydrophobic interior (e.g., resulting from the polymer backbone occupying the interior of the micelle). The unimolecular micelle can be suitably formed by slowly adding a solution of the poly (glycolide) polymer in a water-soluble organic solvent (e.g., acetone) to cold water (e.g., less than about 10° C.) with stirring, followed by in vacuo removal of the solvent. Absent the crosslinks 16, structure 7 of FIG. 2 and structure 1 of FIG. 5a illustrate the unimolecular micelle.

The poly(glycolide) polymer can be further formed into a crosslinked nanoparticle by reacting residual alkynyl groups in the unimolecular micelle with di-triazole organic crosslinking groups. The resulting structure is similar to that of the unimolecular micelle: a unimolecular polymer particle having a substantially hydrophilic exterior and a substantially hydrophobic interior, along with the addition of intramolecular crosslinks in the particle interior (i.e., as illustrated in structure 7 of FIG. 2). Crosslinking has the effect of locking the resulting nanoparticle into a micellar configuration with a hydrophobic interior and a hydrophilic exterior. The degree of crosslinking further affects the rate of release of a drug from the poly(glycolide) polymer to the surrounding environment. More specifically, an increased degree of crosslinking generally reduces the rate of drug release. However, when the degree of crosslinking is greater than about 10% (relative to total functionalization sites in the polymer), the drug hydrolysis rate of triazole-bound drugs is likely to be relatively slow and not further limited by the degree of crosslinking. Thus, a controlled-release composition including the poly(glycolide) polymer and the drug can be designed to release a drug at a desired rate by controlling the degree of crosslinking. In a further refinement, the poly(glycolide) polymer-drug combination can be provided as a plurality of crosslinked nanoparticles with a distribution of crosslinking degrees selected to control the rate of release of an encapsulated component or a covalently bound component in the plurality of crosslinked nanoparticles. For example, a fraction of the plurality can be relatively lightly crosslinked to promote rapid drug release, while another fraction can be relatively highly crosslinked to promote long-term drug release. Suitable degrees of crosslinking (relative to total functionalization sites in the polymer) can range from greater than 0% (i.e., lightly crosslinked) to about 20%, 30%, or 40% (i.e., highly crosslinked), for example about 1% to about 20%, 30%, or 40%, or about 2% to about 15%. For example, when the degree of crosslinking is about 20% and a di-functional organic crosslinker is used, an amount of organic crosslinker equal to about 10% (on a number/molar basis) of the total alkynyl functionalization sites in the original polymer is reacted with the polymer (i.e., thus taking into account that most organic crosslinker molecules will generally be able to form two triazole bonds based on their dual azide functionality). Additionally, different degrees of crosslinking can be associated with different drugs such that a time-dependent drug delivery profile also can be drug-dependent (e.g., a first drug is released from the plurality at a first time after administering the composition and a second (different) drug is released at a second (different) time after administering the composition).

The unimolecular micelles and/or the crosslinked nanoparticles generally have a diameter of about 100 nm or less. The small size is useful in drug-delivery applications, for example facilitating target cell entry and/or biodegradation. For example, the unimolecular micelles generally have a diameter of about 50 nm or less (or about 15 nm to about 50 nm) as measured by dynamic light scattering in aqueous solution. The corresponding crosslinked nanoparticles are generally slightly smaller, having a diameter of about 35 nm or less (or about 8 nm to about 35 nm), also as measured by dynamic light scattering in aqueous solution. Alternatively, the micellar/nanoparticle diameters can be characterized by the TEM measurement of the corresponding dehydrated particles. In this case, the unimolecular micelles and the crosslinked nanoparticles generally have a diameter of about 15 nm or less (or about 2 nm to about 10 nm, for example about 4 nm to about 8 nm) as measured by TEM.

For drug-delivery applications, drugs can be combined with the polymer in a variety of ways. A drug generally includes any chemical administered to a living being (e.g., human patient or other animal) to treat, cure, prevent, and/or diagnose a disease or other physical/mental condition of the living being. As described above, an azide-substituted drug derivative can be covalently bound to the polymer in any of its various forms, for example: (i) a polymer in solution in an organic solvent (e.g., acetone), (ii) a polymer in a unimolecular micellar configuration in an aqueous solution, or (iii) a polymer in a crosslinked nanoparticle configuration. In any of these cases, the drug is covalently bound to the polymer backbone via a triazole link. Additionally, an unmodified (i.e., non-azide substituted) drug can be encapsulated in the hydrophobic interior of a unimolecular micelle. For example, the organic-solvent solution of the poly(glycolide) polymer can additionally contain a drug (e.g., a substantially hydrophobic drug); as the organic solvent is removed from an aqueous solution containing the polymer and the drug, the drug becomes encapsulated within the hydrophobic interior of the forming unimolecular micelle. Once formed, the unimolecular micelle can be further crosslinked while retaining the encapsulated drug within the interior of the resulting crosslinked nanoparticle.

Thus, the foregoing poly(glycolide) polymers can generally be used in a method to deliver a drug compound to a cell (e.g., human (preferable), other animal, plant). The method generally includes (a) providing the drug compound with the poly(glycolide) polymer, and (b) releasing the drug compound to the cell over a period of time. The method can be applied either in vivo or in vitro, and the poly(glycolide) polymer can be either in the form of a unimolecular micelle, a crosslinked nanoparticle, or both (e.g., as an additional manner of controlling drug release rate). The drug compound can be encapsulated by the poly(glycolide) polymer, in the form of a triazole-substituted drug derivative covalently bound to the poly(glycolide) polymer, or both (e.g., when multiple drugs are to be delivered by polymer composition). In an embodiment, the drug compound is in dosage unit form with a carrier.

EXAMPLES

The following Examples illustrate the disclosed compositions and methods, but are not intended to limit the scope of any claims thereto.

In the Examples, the following techniques were used. Polymer molecular weights were determined by GPC-MALS (Multi-Angle Light Scattering) at 35° C. using two PLgel 10μ mixed-B columns in series, and THF as the eluting solvent at a flow rate of 1 mL/min. An Optilab rEX (Wyatt Technology Co.) was used as a detector, calculating absolute molecular weights using a DAWN EOS 18 angle light scattering detector (Wyatt Technology Co.) with a laser wavelength of 684 nm. All samples were filtered through a 0.2 μm Whatman PTFE syringe filter prior to GPC analysis. $^1$H NMR analyses were carried out at room temperature on a Varian UnityPlus-500 spectrometer at 500 MHz or a Varian Unity Plus-300 at 300 MHz referenced to the solvent residual proton chemical shifts. $^{13}$C NMR spectra were obtained on Varian UnityPlus-500 at 125 MHz or a Varian UnityPlus-300 at 75 MHz. UV-vis spectra were recorded with a Cary 300 Bio WinUV, Varian spectrophotometer.

Example 1

Synthesis of Poly(Alkynyl Glycolide) Precursor Polymer

General procedure for bulk polymerizations. Solvent-free polymerizations were carried out in sealed ampoules prepared from ⅜ in. diameter glass tubing that were charged with the monomers and a stir bar, and connected to a vacuum line through a vacuum adapter. After evacuating the ampoule for 4 hours, the ampoule was filled with nitrogen and a syringe was used to add a predetermined amount of tin(II) 2-ethylhexanoate ($Sn(Oct)_2$) and 4-t-butylbenzyl (BBA) alcohol solutions to the ampoule through the adapter. The solvent was removed in vacuo and the ampoule was flame-sealed and immersed in oil bath at 125° C. At the end of the polymerization the ampoule was cooled, opened, and the polymer was dissolved in dichloromethane. A portion of the sample was evacuated to dryness and analyzed by NMR for conversion. The rest of the polymer solution was precipitated from cold methanol.

Representative polymerization of propargyl glycolide. With reference to the structures and synthesis route illustrated in FIG. 2, 2-Hydroxy-4-pentynoic acid ethyl ester (structure 1), 2-hydroxy-4-pentynoic acid (structure 2), 3,6-di-2-propynyl-1,4-dioxane-2,5-dione (structure 3), and poly(propargyl glycolide) (structure 4; "poly(PGL)") were prepared as described in Jiang et al., Macromolecules, 41, 1937-1944 (2008), which is incorporated herein by reference in its entirety. Propargyl glycolide (0.65 g) was polymerized for 45 min of a [M]/[I]=150. The conversion of monomer to polymer calculated from $^1$H NMR was 97%. Precipitation and drying under vacuum gave 0.64 g poly(propargyl glycolide) as a light brown solid (98%). $^1$H NMR ($CDCl_3$) δ 5.31-5.46 (br, 1H), 2.79-3.03 (br m, 2H), 2.01-2.18 (br, 1H). GPC-MALS (THF): $M_n$=31,000 g/mol, PDI=1.28.

Example 2

Synthesis of Unimolecular Micelles

To move from amphiphilic comb polymers to cross-linked nanoparticles, azidoethyl tetraethylene glycol methyl ether was appended to a fraction (e.g., about 75%) of the available alkynyl groups in the poly(PGL) base polymer using the below "click" reaction conditions to give poly($PGL_n$[$EG_yX_{100-y}$]), where n represents the average degree of polymerization, y represents the fraction of pendant alkynes reacted with the azide-functionalized polyoxyethylene, and 100–y represents the remaining fraction of unreacted pendant alkynes. For example, poly($PGL_{124}$[$EG_{75}X_{25}$]) describes a poly(PGL) chain of degree of polymerization 124, and having 75% of its pendant alkynes reacted with the azidoethyl tetraethylene glycol methyl ether (resulting structure 5 in FIG. 2). The azidoethyl tetraethylene glycol methyl ether was formed by tosylating pentaethylene glycol methyl ether and then reacting the product with sodium azide.

General procedure for "click" functionalization. The desired amount of acetylene functionalized polymer, 0.5-0.8 eq. of the azide-substituted polyoxyethylene (relative to the number of available alkynyl groups in the base polymer), and sodium ascorbate powder (12 mol. % with respect to the alkynyl groups) were dissolved in 5 mL DMF in a Schlenk flask, and the solution was deoxygenated by three freeze-pump-thaw cycles. After the solution warmed to room temperature a 0.1 M solution of $CuSO_4.5H_2O$ in deoxygenated DMF (5 mol % with respect to the acetylene groups) was added under nitrogen; the reaction mixture was stirred at room temperature for 3 hours. At the end of the reaction, the solids in the reaction mixture were removed by filtration and ion exchange resin beads (AMBERLITE IRC-748 ion-exchange resin) were added to the solution for 6 hours to remove residual copper. The beads were removed by filtration, the DMF removed in vacuo and the polymer was isolated by dialysis (MWCO=12-14,000) first in an acetone/water (1:1) solution, and then by dialysis in Milli-Q water, and then dried under vacuum.

Poly($PGL_{124}$-[$EG_{75}X_{25}$]). Poly(PGL) (50 mg) ($M_n$, GPC-MALS=23,800 g/mol, PDI=1.10) and azidoethyl tetraethylene glycol methyl ether (0.11 g; 0.75 eq with respect to the alkynyl groups) were dissolved in 5 mL DMF for the click reaction. Poly($PGL_{124}$[$EG_{75}X_{25}$]) was isolated as a viscous liquid (58 mg, 70%).

Formation of unimolecular micelles. A solution of poly ($PGL_{124}$[$EG_{75}X_{25}$]) (20 mg) in 1 mL acetone was slowly added drop-wise to stirred ice-cold Milli-Q water (20 mL) in a Schlenk flask. The solution was allowed to stir for 30 minutes before the acetone was removed in vacuo, thereby forming unimolecular micelles in the remaining water.

Micelle characterization. Micelles were characterized using GPC-MALS, $^1$H NMR, AFM, TEM and Dynamic light scattering (DLS). The results for representative samples are reported below. DLS data were obtained using a temperature-controlled Protein Solutions Dyna Pro-MS/X system. All samples were filtered through a 0.2 μm Whatman PTFE syringe filter and allowed to equilibrate in the instrument for 15 minutes at 25° C. before measurements were taken. The uniformity of the particle sizes were determined by a monomodal curve fit, which assumes a single particle size with a Gaussian distribution.

Surface profile measurements were performed with a Pacific Nanotechnology Nano-R atomic force microscope in close contact (oscillating) mode to generate height images that were not altered other than a simple leveling procedure. Silicon tips with a spring constant of 36 N/m, tip curvature of 10-20 nm, and a resonance frequency of 286-339 kHz were used for all experiments. The nanoparticles were dispersed in Milli-Q water and the solutions (typical concentration, 20-300 μg/ml) were spin coated at 5000 rpm for 40 sec on the silicon substrate.

Transmission electron microscopy samples (typical concentration, 20-300 μg/mL) were dropped onto nickel grids pretreated with FORMVAR resin and allowed to settle for 2 min before removing the excess solution. The sample was negatively stained with either a 1% phospho-tungstic acid (PTA) stain or 2% uranyl acetate (UA) stain prepared with deionized water. Micrographs were collected at 270,000-370,000× magnification on a JEOL 100CX TEM.

Figure 3A:
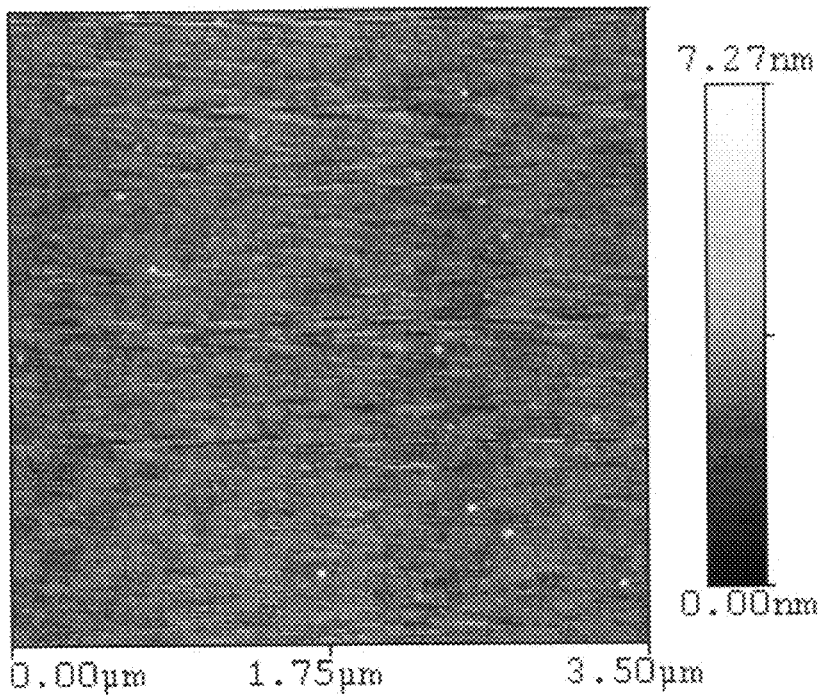
FIG. 3a is an AFM image of unimolecular micelles prepared by spin-coating a 0.20 mg/ml solution onto a silicon wafer.
Figure 3B:
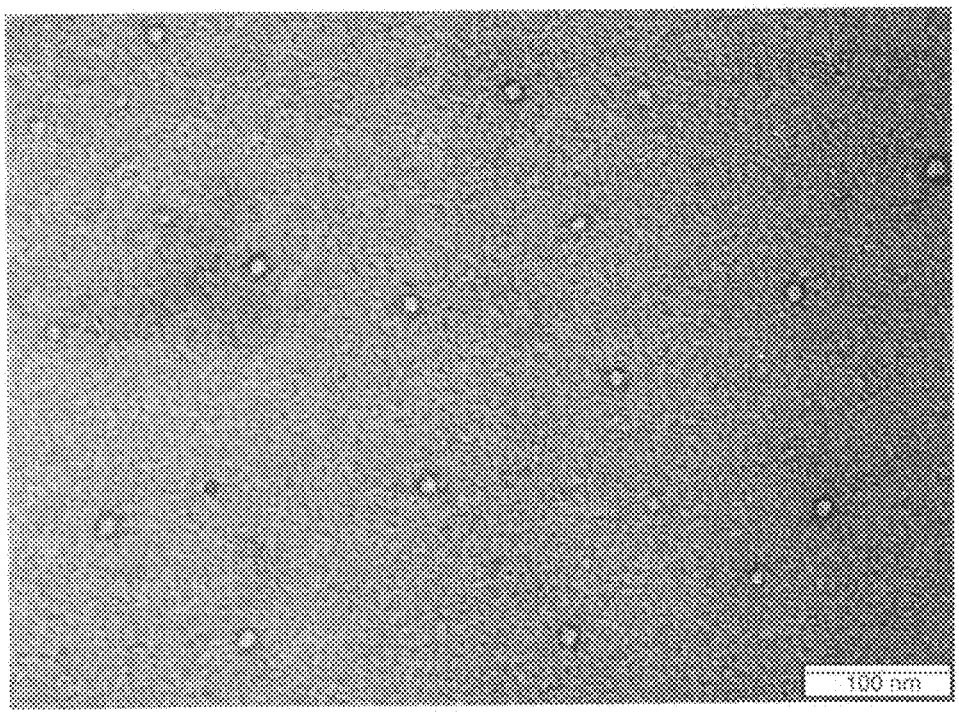
FIG. 3b is a TEM (transmission electron microscope) image of unimolecular micelles deposited from a 0.20 mg/ml solution onto a FORMVAR resin-coated Ni grid and allowed to settle for 2 min before removing the excess solution. The sample was negatively stained with 1% phosphotungstic acid; scale bar=100 nm.

Various poly(glycolide) polymers according to the disclosure were formed by reacting poly(PGL) with azidoethyl tetraethylene glycol methyl ether to form polymers of variable molecular weight and fractional conversion of alkynyl groups to triazole-linked hydrophilic organic groups. The polymers were then formed in into unimolecular micelles. The characteristics of the various resulting unimolecular micelles are summarized in Table 1. Additionally, FIGS. 3a and 3b are AFM and TEM images, respectively, of a sample of unimolecular micelles (polymer 2a from Table 1 below).

TABLE 1

Micelle Characterization Data

| Polymer | $M_n$ poly(PGL)[a] | PDI[a] | $N_{alkyne}$[b] | $M_n$ poly(PGL$_n$[EG$_N$X$_{1-N}$])[a] | $R_h$ (nm)[c] | Height$_{avg}$ (nm)[d] |
|---|---|---|---|---|---|---|
| 1a | 10,000 (n ≈ 52) | 1.19 | 74 | 31,300 | 35 ± 2 | 3.2 ± 0.1 |
| 2a | 23,800 (n ≈ 124) | 1.30 | 85 | 69,000 | 35 ± 2 | 3.0 ± 1 |
| 3a | 31,000 (n ≈ 161) | 1.28 | 66 | 90,000 | 37 ± 2 | 3.0 ± 0.1 |

[a]determined by GPC-MALS using THF as the eluting solvent at 35° C.; parenthetical value for n of poly(PGL) represents approximate degree of polymerization using a MW = 192 for the propargyl glycolide repeating unit.
[b]percent of alkynyl groups reacted with azide-substituted polyoxyethylene, determined by NMR spectroscopy.
[c]hydrodynamic radius, determined by dynamic light scattering at 25° C.
[d]determined by AFM; 0.20 mg/mL solution spin coated in Si wafer.

Example 3

Synthesis of Crosslinked Nanoparticles

Figure 4A:
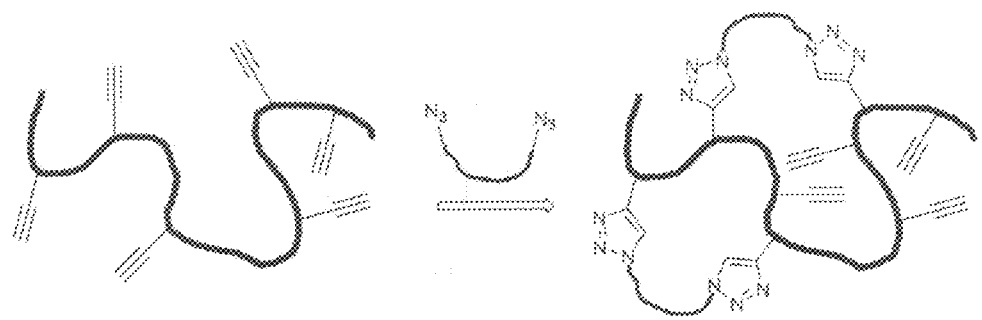
FIG. 4a illustrates the crosslinking reaction of FIG. 2 (pendant hydrophilic organic groups omitted for clarity).
Figure 4B:
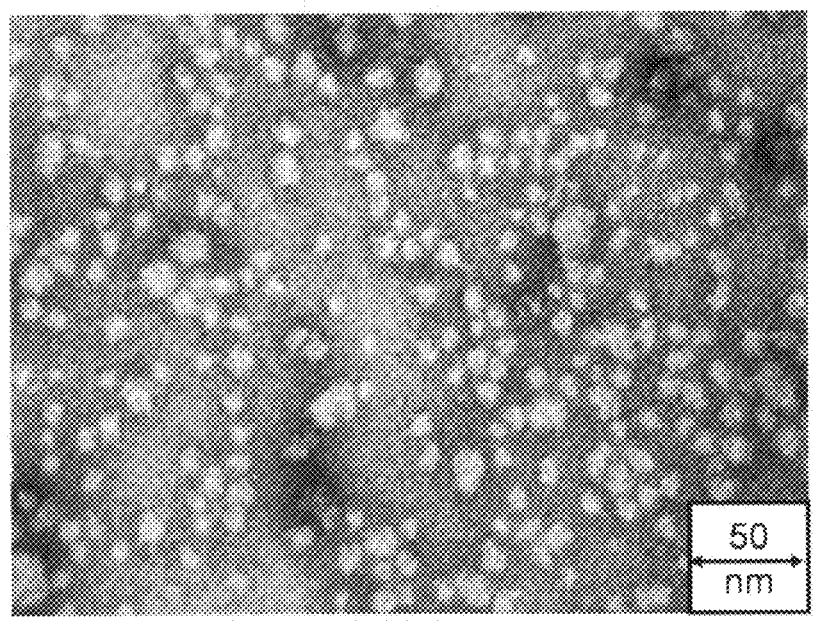
FIG. 4b is a TEM image of crosslinked nanoparticles (click reaction products of poly(propargyl glycolide) (72,000 g/mol) with 1,5-diazidopentane) that were deposited onto a FORMVAR resin-coated nickel grid from a 0.25 mg/ml aqueous solution, and negatively stained with phosphotungstic acid after solvent removal.
Figure 4C:
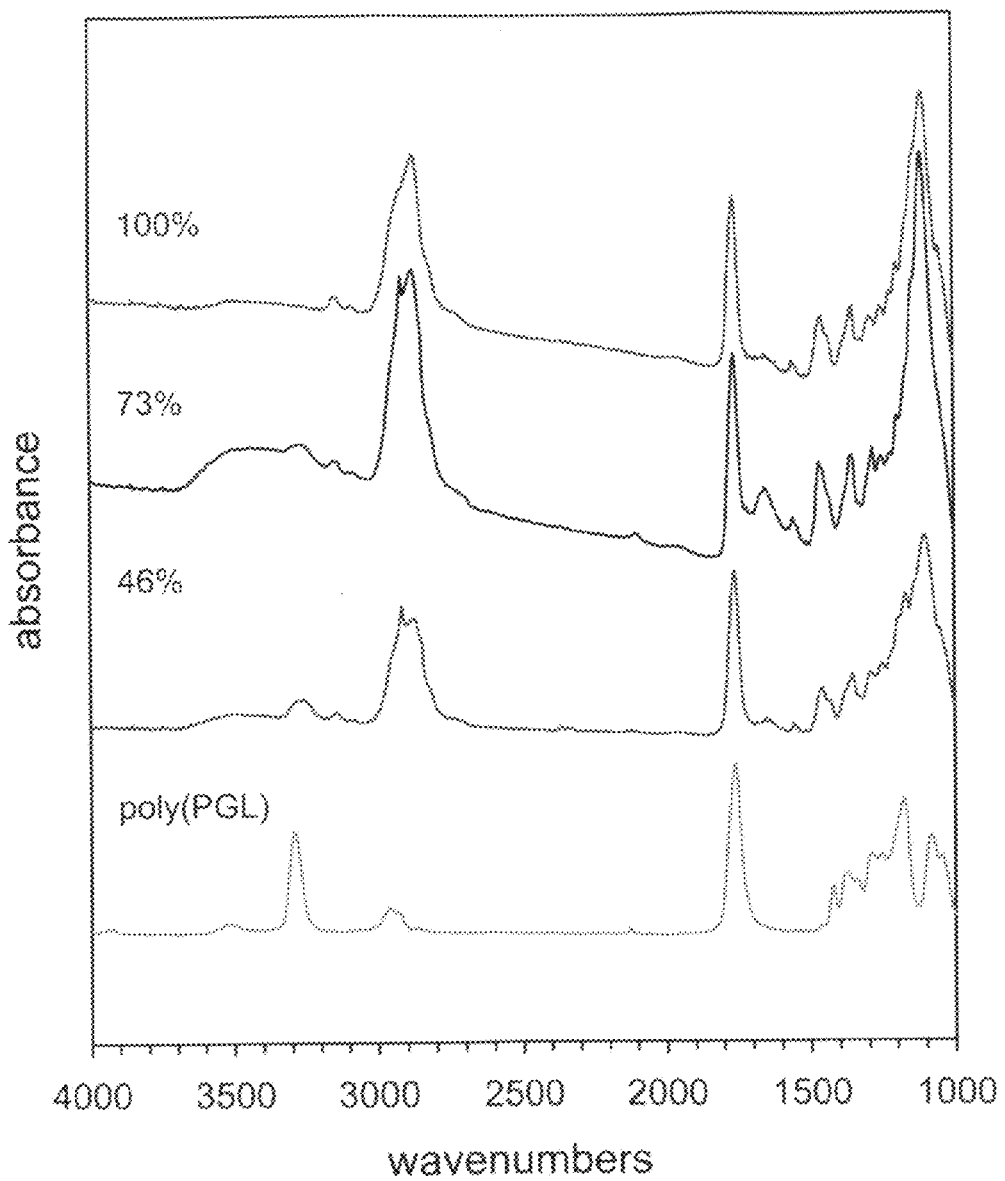
FIG. 4c illustrates the IR spectra of crosslinked nanoparticles as a function of % crosslinking of free alkynyl groups after functionalization with a polyoxyethylene azide (% crosslinking degrees of 0% ("poly(PGL)"), 46%, 73%, and 100%).
Figure 4D:
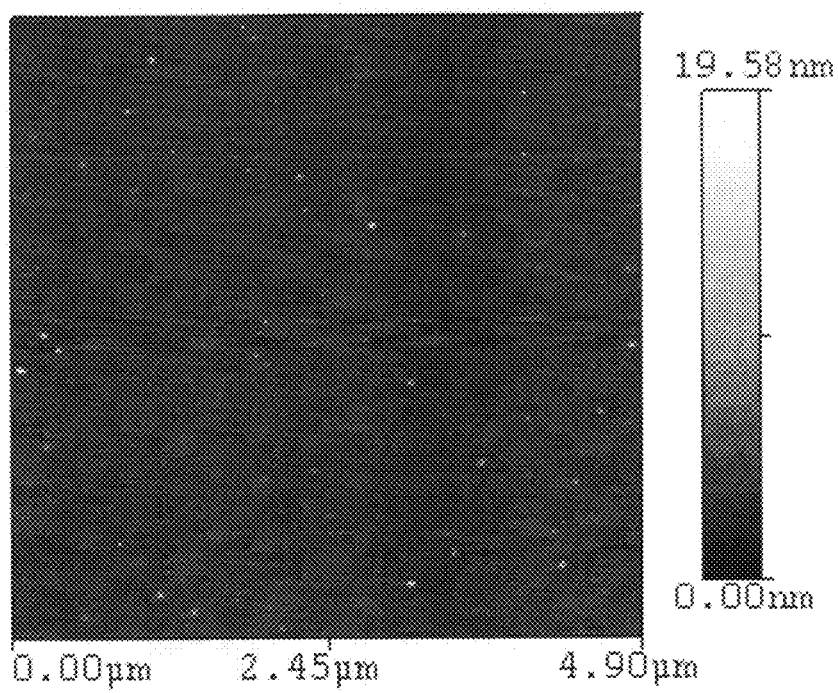
FIG. 4d is an AFM (atomic force microscope) image of crosslinked nanoparticles prepared by spin-coating a 0.20 mg/ml solution onto a silicon wafer.
Figure 4E:
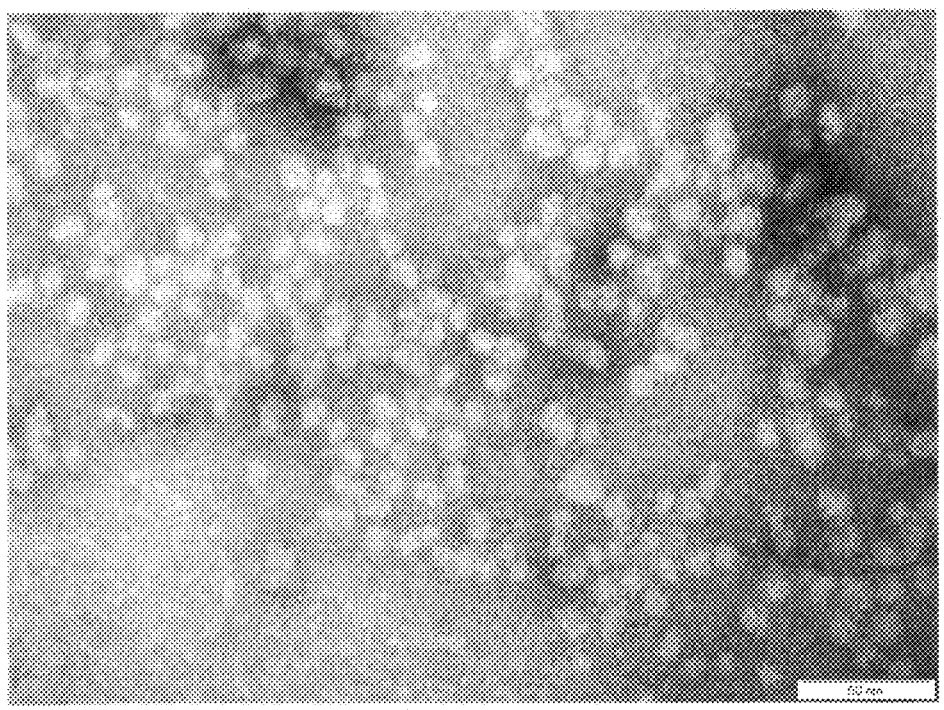
FIG. 4e is a TEM image of crosslinked nanoparticles deposited from a 0.20 mg/ml solution (370,000× magnification; scale bar=100 nm).

Cross-linking was effected by dissolving the polymer in a minimal amount of acetone followed by drop-wise addition of the solution to stirred Milli-Q water. The acetone was removed in vacuo, and then cross-linked nanoparticles were formed by coupling 1,5-diazidopentane to the residual alkynes of the poly(PGL) base polymer, as schematically illustrated in FIG. 4a. The progress of the crosslinking reaction was monitored by following the disappearance of the alkyne stretching band in the IR spectrum (FIG. 4c). NMR analysis of the particles following their purification by dialysis, first in an acetone/water solution and then by dialysis in Milli-Q water, showed no evidence for residual azides or alkynyl groups. Thus, substantially all of the original alkynyl groups in the poly(alkynyl glycolide) precursor polymer (i.e., poly(PGL) in this case) were consumed/functionalized in the final crosslinked nanoparticles. FIG. 4b shows a TEM image of the cross-linked nanoparticles; further AFM/TEM images are shown in FIGS. 4d and 4e. Given the polymer molecular weight of 72,000 g/mol ("polymer 2c") and assuming a spherical shape and a density of 1.0 g/cm³ for a dried particle, a fully dense particle was calculated to have a 6 nm diameter, consistent with the 6±2 nm diameter-seen in TEM. While the agreement may be somewhat fortuitous, their uniformity is consistent with particles derived from individual polymer chains.

Core cross-linked nanoparticles. A round bottom flask equipped with a magnetic stir bar and charged with poly (PGL$_{124}$[EG$_{75}$X$_{25}$]) micelles (20 mL of 0.20 mg/mL solution) and sodium ascorbate (1 eq with respect to the remaining acetylene groups) and CuSO$_4$.5H$_2$O (0.5 eq with respect to the remaining alkynyl groups), and then placed under nitrogen. The solution was allowed to stir 5 min and then a solution of 1,5-diazidopentane (10-100 mol. % with respect to the remaining alkynyl groups) dissolved in 1 mL acetone was slowly added drop-wise. The solution was allowed to stir under nitrogen 2 d, and was then condensed and dissolved in 5 mL of DMF. Amberlite IRC-748 ion-exchange resin beads were added, and, after 6 h, the beads were removed, and the solution was transferred to presoaked dialysis tubing (MWCO ca. 12-14 kDa). The polymer was purified by dialysis first in an acetone/water (1:4) solution and then by dialysis in Milli-Q water.

As illustrated in FIG. 4c, the disappearance of the alkyne C—H stretch (3340-3270 nm) and the appearance of the triazole stretch (N—H) (3300-2500 nm) were observed using infared spectroscopy. IR spectroscopy also confirmed that no additional azide groups (2100 nm) were present. The spectra of poly(PGL) and poly(PGL$_{124}$[EGyX$_{100-y}$]), with varying degrees of functionalization were taken with Mattson Galaxy 3000 FT-IR.

Various crosslinked nanoparticles according to the disclosure were formed by reacting the unimolecular micelles with 1,5-diazidopentane to form polymers of variable molecular weight and degrees of crosslinking. The polymers were then formed in into unimolecular micelles. The characteristics of the various resulting crosslinked nanoparticles are summarized in Table 2. In Table 2, polymers 1b, 2b, and 3b are the crosslinked analogs to polymers 1a, 2a, and 3a in Table 1, respectively, and the Mn values are listed prior to crosslinking.

TABLE 2

Nanoparticle Characterization Data

| Polymer | $Mn^a$ poly(PGL$_n$[EG$_y$X$_{100-y}$]) | % cross-linked[b] | $R_h$ (nm)[c] | $H_{avg}$ (nm)[d] |
|---|---|---|---|---|
| 1b | 31,300 | 50 | 18 ± 2 | 4.5 ± 0.3 |
| 2b | 69,000 | 100 | 12 ± 2 | 6.0 ± 1 |
| 3b | 90,000 | 10 | 39 ± 2 | 3.5 ± 0.8 |

[a]determined by GPC-MALS using THF as the eluting solvent at 35° C.
[b]percent of remaining alkynes that were cross-linked by 1,5-diazidopentane; determined by initial feed ratio.
[c]hydrodynamic radius, determined by dynamic light scattering at 25° C.
[d]determined by AFM; 0.20 mg/mL solution spin coated in Si wafer.

Estimation of cross-linked nanoparticle size. One polymer, $M_n$=72,000 g/mol (from GPC)×1 mol/6.02×10$^{23}$ chains=1.19×10$^{-19}$ g. Assume the polymer can be approximated as a sphere of density (ρ)=1 g/cm³ Mass of a dense particle=V×ρ=(4/3)πr³×1 g/cm³=1.13×10$^{-19}$ g. Diameter of a 1.13×10$^{-19}$ gparticle with ρ=1 g/cm³=2×radius= ((3/4)V/π)$^{1/3}$ 1 nanoparticle≈6 nm.

Example 4

Covalent Attachment of Small Molecules to Micelles and Nanoparticles

A question with any cross-linking protocol is the success and degree of crosslinking in the particles. To answer this question and to explore the possibility of loading crosslinked unimolecular micelles with covalently attached biologically relevant drugs, an azido-substituted drug surrogate was covalently attached to the synthesized polymer. Specifically, 3-azido-7-hydroxycoumarin, a dye precursor that transforms to a fluorescent dye after undergoing a 1,3-dipolar cycloaddition reaction[27], was used as the surrogate. As illustrated in FIG. 5a, two click reactions paths using poly(PGL$_{124}$ [EG$_{75}$X$_{25}$]) as the substrate and the dye precursor were considered. The first reaction (path "a" in FIG. 5a) evaluated the potential for covalent attachment of small molecules, and the second reaction (path "b" in FIG. 5a) probed the extent of crosslinking using an excess of the dye precursor to react with residual alkynyl groups in the nanoparticles. This is important for drug delivery, because residual alkynyl groups represent potential site of drug attachment. The relative dye loadings were interrogated by measuring the fluorescence intensities of $1 \times 10^{-6}$ M nanoparticle solutions. The results indicate that the nanoparticles can be loaded with a covalently bonded triazole-substituted drug derivative after being formed into crosslinked nanoparticles, and the efficiency of the click functionalization was determine based on the number residual alkynyl groups after functionalization.

Figure 5B:
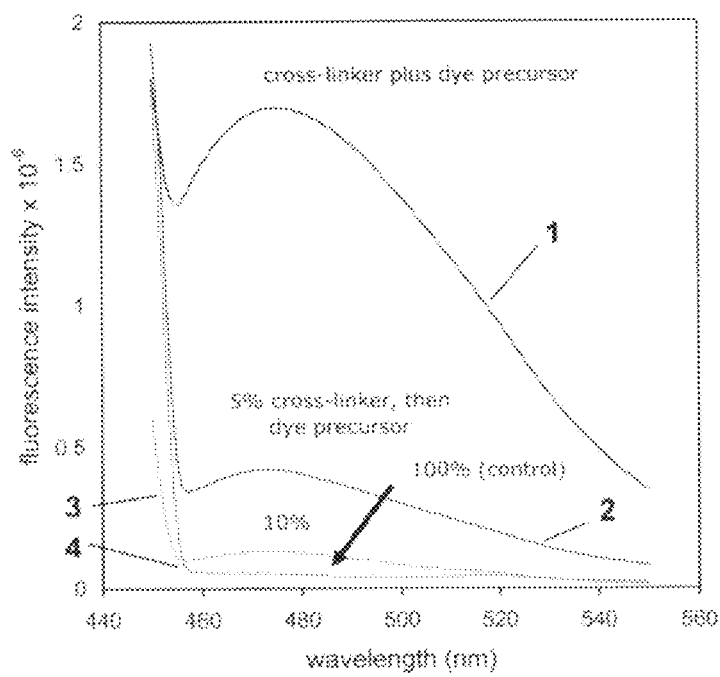

Covalent attachment of 3-azido-7-hydroxycoumarin to nanoparticles. Using poly($PGL_{124}[EG_{75}X_{25}]$) as the substrate and the conditions described earlier, two reactions were performed: (1) a single click step using an equimolar mixture of the dye precursor and 1,5-diazidopentane (path "a" in FIG. 5a); and (2) a two-step process where 5%, 10%, or 100% of the remaining alkynyl groups of poly($PGL_{124}[EG_{75}X_{25}]$) were first click-crosslinked with 1,5-diazidopentane, followed by a second click reaction using an excess of the dye precursor (path "b" in FIG. 5a). The nanoparticle fluorescence was recorded using a Fluorolog-3 (Instruments S.A., Inc.) fluorometer. All samples were diluted to $1 \times 10^{-6}$ M using Milli-Q water, excited at $\lambda_{ex}$=440 nm, and the fluorescence emission was observed from 450-500 nm. FIG. 5b illustrates the fluorescence intensity of the following 1-step and 2-step click reactions on poly($PGL_{124}[EG_{75}X_{25}]$) substrates: a single click step using an equimolar mixture of the dye precursor and 1,5-diazidopentane (blue; line 1); a two step process where 5% of the remaining alkynyl groups were crosslinked, followed by a second click reaction using an excess of the dye precursor (red; line 2); the same protocol with 10% crosslinking (orange; line 3); and the same protocol with 100% crosslinking (green; line 4).

Example 5

Drug Encapsulation by Unimolecular Micelles

Figure 6:
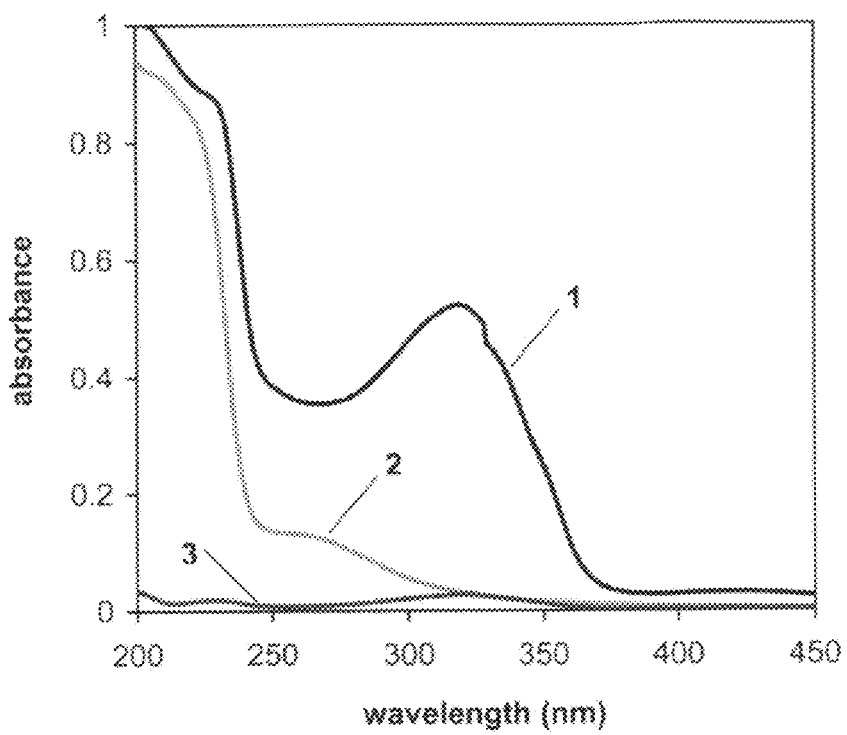
FIG. 6 illustrates the UV-vis spectra of: azobenzene-loaded unimolecular polymeric micelles (blue; line 1), unimolecular polymeric micelles (green; line 2), and azobenzene in water (red; line 3).

Controlled drug release improves drug efficacy, reduces toxicity and improves patient compliance and convenience.[28] A similar protocol was used to evaluate encapsulation of hydrophobic molecules in nanoparticles. Poly($PGL_{124}[EG_{75}X_{25}]$) and azobenzene, a drug surrogate, were dissolved in a minimal amount of acetone, and dispersed in Milli-Q water. After removal of the acetone in vacuo, unimolecular micelles were formed, and the encapsulation of azobenzene in the micelles was confirmed by azobenzene's characteristic absorbance at 320 nm, as illustrated in FIG. 6. Specifically, FIG. 6 illustrates the UV-vis spectra of: azobenzene-loaded unimolecular polymeric micelles (blue; line 1), unimolecular polymeric micelles (green; line 2), and azobenzene in water (red; line 3).

Example 6

Drug Encapsulation by Crosslinked Nanoparticles

Figure 7:
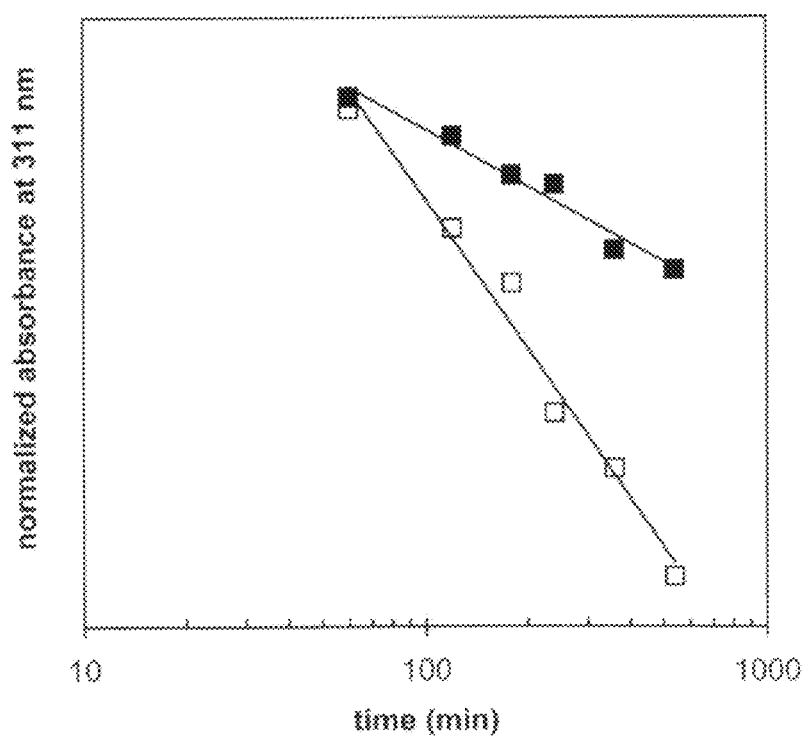
FIG. 7 illustrates the controlled released of azobenzene from azobenzene-loaded crosslinked nanoparticles (solid squares) and azobenzene-loaded unimolecular polymeric micelles (open squares) suspended in water at room temperature over about 10 hours.

The drug encapsulation experiment of Example 5 was repeated, but this time using click chemistry to crosslink the azobenzene-loaded unimolecular polymeric micelles with 1,5-diazidopentane, thereby forming azobenzene-loaded crosslinked nanoparticles. To track the release of azobenzene from the particles, crosslinked nanoparticle solutions were placed in dialysis tubing (MWCO=12-14 kDa) and dialyzed with Milli-Q water. Removing aliquots of the nanoparticle solution from dialysis bag and measuring their UV-vis spectra allowed monitoring of the continuous release of encapsulated azobenzene over 10 hours. As shown in FIG. 7, the azobenzene release rate from the cross-linked nanoparticles was about the rate measured for a non-crosslinked control (i.e., non-crosslinked unimolecular polymeric micelles). These data are consistent with successful crosslinking, and suggest that an ensemble of particles having different degrees of crosslinking can be the basis of a drug-release composition that maintains long-term controlled release strategy.

Example 7

Biocompatibility of Crosslinked Nanoparticles

Figure 8A:
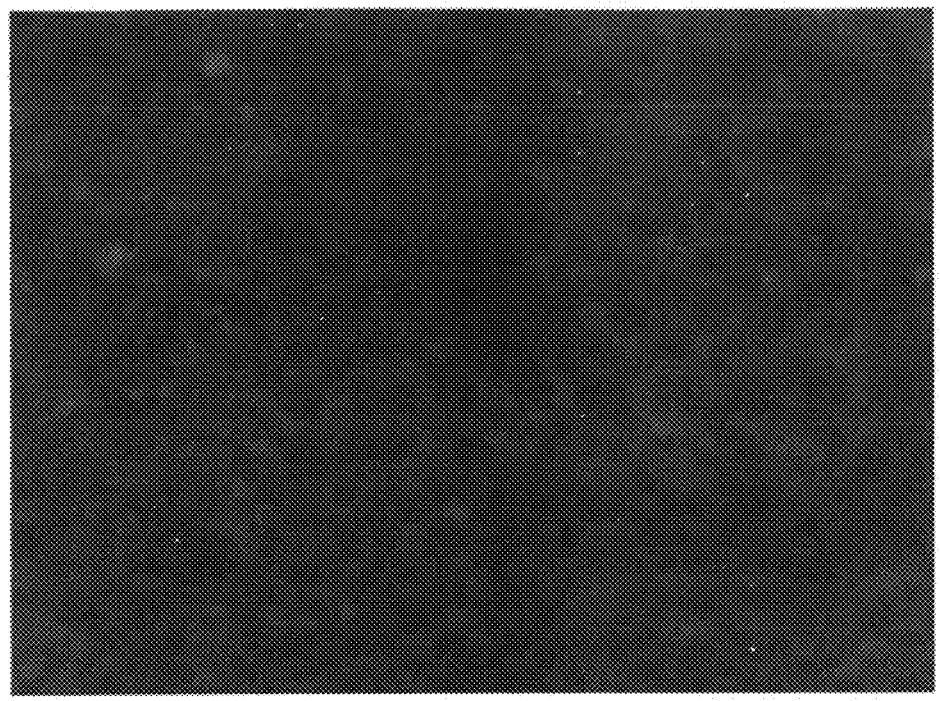
FIG. 8a illustrates cortical astrocytes cultured in media containing 10 μg/ml of crosslinked nanoparticles for 24 hours.

For in vivo applications, nanoparticles must be biocompatible and degradable. In a single click reaction, poly($PGL_{124}[EG_{75}X_{25}]$) was crosslinked and a rhodamine dye was appended to the nanoparticles. After dialysis to remove residual dye and click reagents, cortical astrocytes were cultured in a 10 µg/mL solution of dye-labeled nanoparticles. After 24 hours, the cells were washed to remove particles that had not entered the cells and then imaged by confocal microscopy. FIG. 8a illustrates cortical astrocytes cultured in media containing 10 µg/ml of crosslinked nanoparticles for 24 hours. In FIG. 8a, the red color emanates from rhodamine dye covalently linked to the nanoparticles that have entered cells. FIG. 8a shows that the nanoparticles readily entered the cells, probably due to their small size and their polyoxyethylene exterior, which screens particle/protein interactions. The cells remained healthy for more than 30 days and showed no signs of nanoparticle toxicity.

Figure 8B:
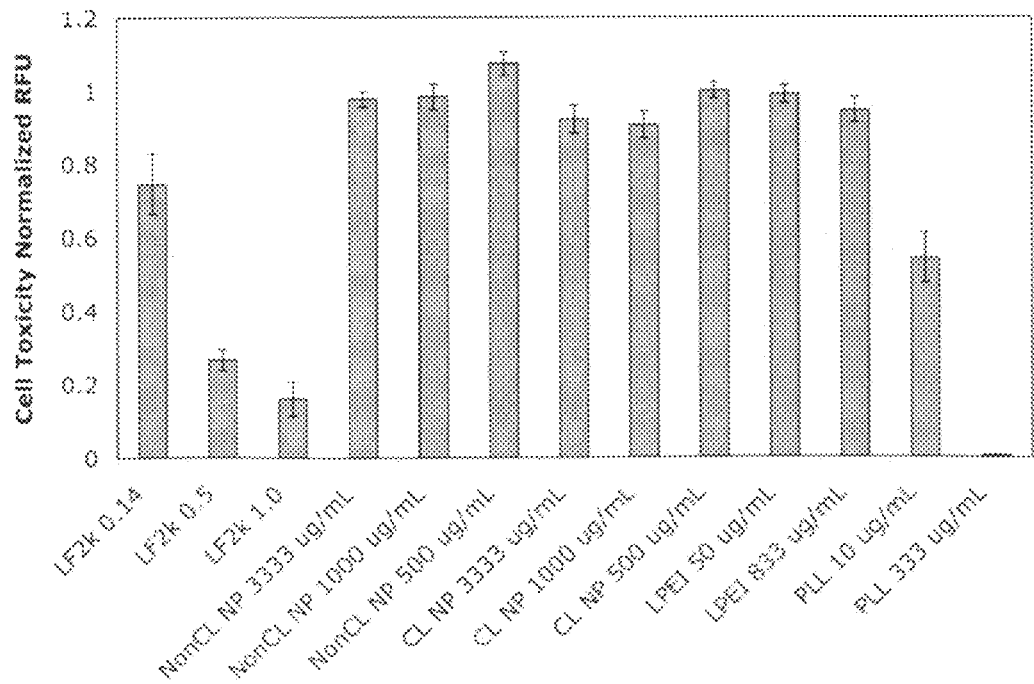
FIG. 8*b* compares the cell toxicity (in normalized relative fluorescence units) for various nanoparticle solutions both according to the disclosure and using commercially available reference nanoparticles.

These data are in agreement with the viability assays on various crosslinked nanoparticles, which show no detectable toxicity for nanoparticle concentrations up to about 3000 µg/mL, as illustrated in FIG. 8b. Specifically, HeLa cells were plated in 96-well black-clear bottom plates at 10,000 cells/well in 100 µL of culture medium lacking antibiotic and grown for 22 hr at 37° C. Cells were about 70%-80% confluent based on microscopy. Nanoparticle solutions were prepared in OptiMEM (Invitrogen) when dilutions were required (50 µl total volume) and added to the 100 µL of culture medium. Cells were incubated for an additional 22 hr and then 20 µL Cell Titer Blue (CTB) reagent was added. Fluorescence was quantified in a fluorescence plate reader 2 hr after CTB reagent was added, according to the manufacturer's instructions. Results are reported as the average±standard deviation (n=3). Non-crosslinked nanoparticles (poly($PGL_{124}[EG_{75}X_{25}]$; unimolecular micelles or "NonCL NP" as referenced in FIG. 8b) and crosslinked nanoparticles (poly($PGL_{124}[EG_{75}X_{25}]$ with 10% cross-linking of remaining alkynyl groups; "CL NP") correspond to polymers mentioned in the text. LipoFectamine ("LF2k"), linear poly (ethylene imine) ($M_n$=25,000; "LPEI"), and poly(L-lysine) ($M_n$=150,000; "PLL") were used as controls. LF2k is reported as dilutions of the purchased solution. FIG. 8b compares the cell toxicity (in normalized relative fluorescence units) for the foregoing nanoparticles at varying concentrations.

Example 8

Hydrolytic Degradation of Functionalized Poly(glycolide)

Figure 9:
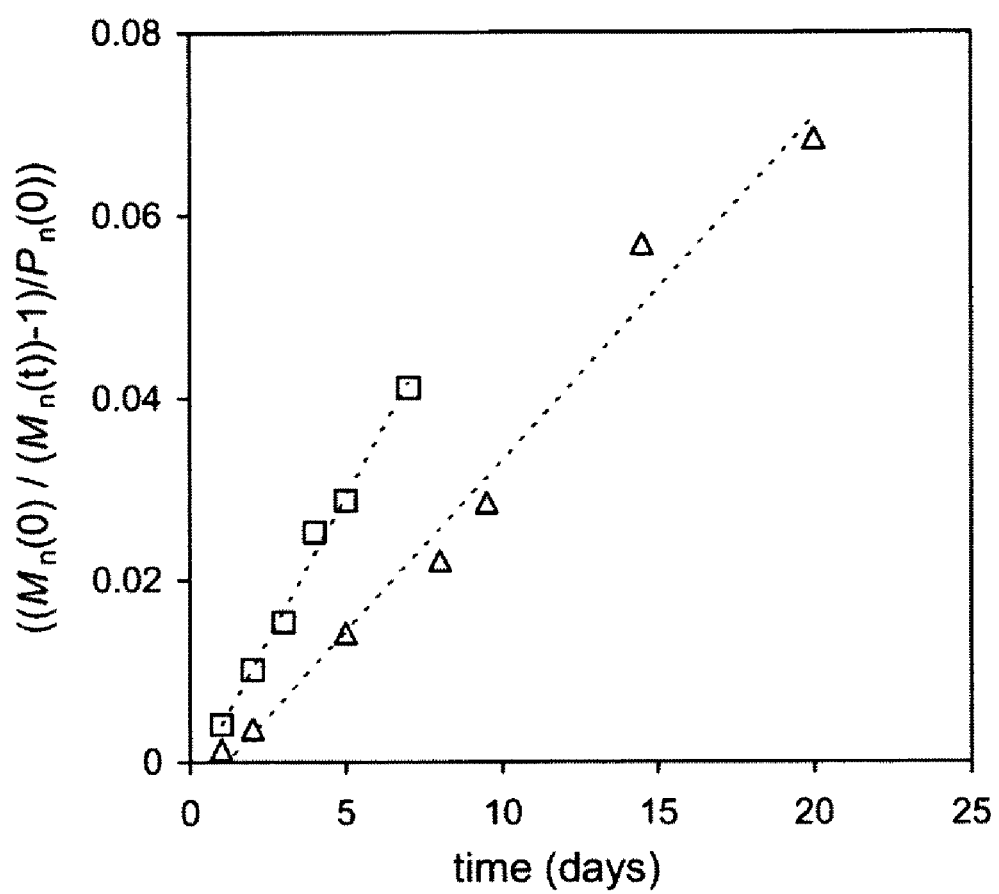
FIG. 9 compares the relative rates of hydrolytic degradation of polyoxyethylene-functionalized poly(propargyl glycolide) (open squares) and rac-lactide (open triangles) by measuring the molecular weight as a function of time.

Poly(glycolide) and related polymers are susceptible to hydrolytic degradation. Degradation experiments were performed at 36° C. in Milli-Q water, and the measured molecular weights were plotted in FIG. 9 (open squares: poly (PGL$_{124}$[EG$_{75}$X$_{25}$]); open triangles: rac-poly(lactide). The molecular weights according to the random chain scission model (i.e., (M$_n$(0)/M$_n$(t)−1)/P$_n$(0) versus time, where P$_n$(0) is the initial degree of polymerization) were also plotted in FIG. 9 (dashed lines). The polyoxyethylene-functionalized poly(propargyl glycolide) degrades more rapidly than rac-lactide, as shown in FIG. 9. Accordingly, combinations of the two polymers (e.g., as random or block copolymers) can be used to control the rate of degradation.

Degradation of poly(PGL$_{124}$[EG$_{75}$X$_{25}$]). 10 mg samples of non-crosslinked poly(PGL$_{124}$[EG$_{75}$X$_{25}$]) were placed in 20 mL culture tubes, and 10 mL of Milli-Q water was added. The tubes were capped and placed in a degradation chamber at 36° C. Samples were removed at predetermined times, dried, and the molecular weight was determined by GPC-MALS. For comparison, a similar experiment was run looking at the degradation of rac-lactide; however, the experiment was run at 55° C. to accelerate degradation. The results were normalized to account for the initial degree of polymerization (P$_n$(0)) of each polymer.

Example 9

Synthesized Crosslinked Nanoparticle Compositions

The various azide-substituted functional groups generally described above (and those specifically illustrated in FIG. 10) can be incorporated into a poly(glycolide) polymer. Several crosslinked nanoparticle compositions have been synthesized according to the disclosure to illustrate the variety of functional groups (and the variety in the levels of incorporation of the functional groups) that can be added to a poly(glycolide) polymer backbone having alkynyl functionality via the click chemistry mechanism. Table 3 presents the composition of the synthesized nanoparticle compositions.

TABLE 3

Crosslinked Nanoparticle Compositions

| ID | Composition |
| --- | --- |
| V.18 | PG$_{131}$[(C$_1$EO$_4$C$_2$)$_{80}$CL$_{20}$] |
| V.32 | PG$_{65}$[PEG$_{63}$Rh$_4$CL$_{33}$] |
| V.92 | PG$_{177}$[PEG$_{48}$CL$_{25}$] |
| V.93 | PG$_{177}$[PEG$_{30}$A1$_{20}$CL$_{25}$] |
| V.121 | PG$_{300}$[PEG$_{47}$C10$_{32}$CL$_{20}$] |
| VII.22 | PG$_{157}$[PEG$_{80}$CL$_{10}$] |
| VII.108 | PG$_{300}$[PEG$_{37.5}$LC$_{37.5}$CL$_{24}$] |
| VII.126 | PG$_{300}$[PEG$_{30}$LC$_{30}$CL$_{25}$] |

Figure 11:
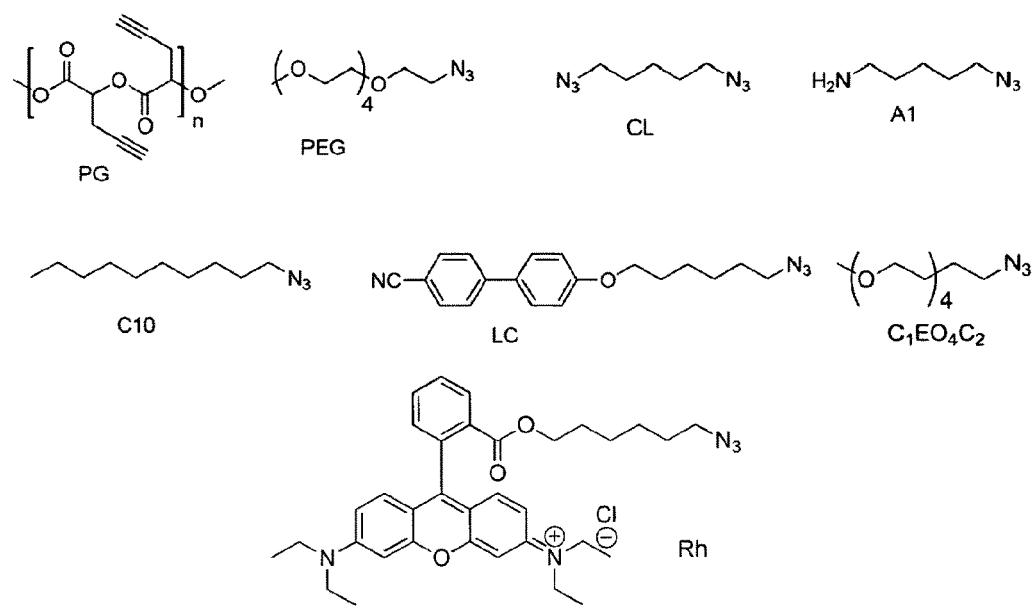
FIG. 11 illustrates specific chemical structures of azide-substituted organic compounds used to form crosslinked poly(glycolide) polymer nanoparticles.

For the compositions in Table 3, the polymer (PG) was first synthesized according to the general procedure outlined in the above examples. The ligands (PEG, CL, A1, C10, LC, C$_1$EO$_4$C$_2$, and Rh) were then added to polymer chain, also as described above. The structures of the specific polymer and ligands are illustrated in FIG. 11. The formulae in Table 3 describe the composition of the particles. For example, nanoparticle V.93 is a poly(propargyl glycolide) with 177 repeat units, and PEG$_{30}$A1$_{20}$CL$_{25}$ denotes that 30% of the pendent alkynes of the polymer were reacted with the PEG-based azide, 20% with the amine A1, and 25% of the pendent alkynes of the polymer were reacted with the crosslinker CL. Some polymers were partially modified, meaning that some alkynyl groups remained unreacted in the nanoparticle (e.g., VII.22 has 80% PEG, 10% CL, and the remaining 10% of the alkynyl groups in the original PG polymer remain unreacted in the nanoparticle). The Rh groups in the nanoparticles act as markers. Specifically, the Rh dye is released from the nanoparticle in an aqueous environment (i.e., allowing the time-release properties of the nanoparticles to be monitored, for example in relation to a triazole-linked drug to be delivered by a nanoparticle). Liquid crystal mesogens can be added to the nanoparticles to act as a visible marker that remains attached to the nanoparticle in an aqueous environment (i.e., allowing the mobility properties of the nanoparticles to be monitored).

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

Throughout the specification, where the compositions, processes, or apparatus are described as including components, steps, or materials, it is contemplated that the compositions, processes, or apparatus can also comprise, consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure.

References (1) Liu, Y. Y.; Miyoshi, H.; Nakamura, M. Int. J. Cancer 2007, 120, 2527-2537.
(2) Couvreur, P.; Puisieux, F. Adv. Drug Deliv. Rev. 1993, 10, 141-162.
(3) Duncan, R. Nat. Rev. Drug Discov. 2003, 2, 347-360.
(4) Jin, S.; Ye, K. M. 2007, 23, 32-41.
(5) Hawker, C. J.; Wooley, K. L. Science 2005, 309, 1200-1205.
(6) Newkome, G. R.; Moorefield, C. N.; Baker, G. R.; Saunders, M. J.; Grossman, S. H. Angew. Chem.-Int. Edit. Engl. 1991, 30, 1178-1180.
(7) Lawrence, M. J. Chem. Soc. Rev. 1994, 23, 417-424.
(8) Wooley, K. L. J. Polym. Sci. Pol. Chem. 2000, 38, 1397-1407.
(9) Kataoka, K.; Harada, A.; Nagasaki, Y. Adv. Drug Deliv. Rev. 2001, 47, 113-131.
(10) Emoto, K.; Iijima, M.; Nagasaki, Y.; Kataoka, K. J. Am. Chem. Soc. 2000, 122, 2653-2654.
(11) Butun, V.; Lowe, A. B.; Billingham, N.C.; Armes, S. P. J. Am. Chem. Soc. 1999, 121, 4288-4289.
(12) Iijima, M.; Nagasaki, Y.; Okada, T.; Kato, M.; Kataoka, K. Macromolecules 1999, 32, 1140-1146.
(13) Butun, V.; Billingham, N.C.; Armes, S. P. J. Am. Chem. Soc. 1998, 120, 12135-12136.
(14) Schartl, W. Adv. Mater. 2000, 12, 1899-+.
(15) O'Reilly, R. K.; Joralemon, M. J.; Wooley, K. L.; Hawker, C. J. Chem. Mat. 2005, 17, 5976-5988.
(16) Joralemon, M. J.; O'Reilly, R. K.; Hawker, C. J.; Wooley, K. L. J. Am. Chem. Soc. 2005, 127, 16892-16899.
(17) Blomberg, S.; Ostberg, S.; Harth, E.; Bosman, A. W.; Van Horn, B.; Hawker, C. J. J. Polym. Sci. Pol. Chem. 2002, 40, 1309-1320.

(18) Harth, E.; Van Horn, B.; Lee, V. Y.; Germack, D. S.; Gonzales, C. P.; Miller, R. D.; Hawker, C. J. J. Am. Chem. Soc. 2002, 124, 8653-8660.
(19) Croce, T. A.; Hamilton, S. K.; Chen, M. L.; Muchalski, H.; Harth, E. Macromolecules 2007, 40, 6028-6031.
(20) Jiang, X.; Vogel, E.; Baker, G. L.; Smith, M. R., III J. Polym. Sci., Part A, Polym. Chem. 2007, 45, 5227-5236.
(21) Jing, F.; Smith, M. R., III; Baker, G. L. Macromolecules 2007, 40, (in press, DOI:10.1021/ma071430d).
(22) Liu, T. Q.; Simmons, T. L.; Bohnsack, D. A.; Mackay, M. E.; Smith, M. R., III; Baker, G. L. Macromolecules 2007, 40, 6040-6047.
(23) Yin, M.; Baker, G. L. Macromolecules 1999, 32, 7711-7718.
(24) Simmons, T. L.; Baker, G. L. Biomacromolecules 2001, 2, 658-663.
(25) Jiang, X.; Smith, M. R., III; Baker, G. L., (in press, DOI: 10.1021/ma070775t).
(26) Jiang, X.; Vogel, E. B.; Milton R. Smith, I.; Baker, G. L. Macromolecules 2008, 41, 1937-1944.
(27) Sivakumar, K.; Xie, F.; Cash, B. M.; Long, S.; Barnhill, H. N.; Wang, Q. Org. Lett. 2004, 6, 4603-4606.
(28) Uhrich, K. E.; Cannizzaro, S. M.; Langer, R. S.; Shakesheff, K. M. 1999, 99, 3181-3198.

What is claimed is:

1. A poly(glycolide) polymer comprising: a triazole reaction product of
(a) an alkynyl glycolide according to Formula III

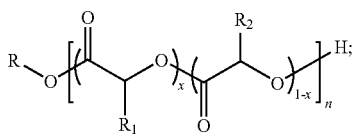

[Formula III]

(b) an azide-substituted hydrophilic organic compound; and,
(c) optionally one or more of an azido organic crosslinker, an azide-substituted hydrophobic organic compound, an azide-substituted liquid crystal mesogen, an azide-substituted dye, and an azide-substituted drug;
wherein:
(i) $R_1$ comprises one or more moieties selected from a hydrogen, an alkyl group, and an alkynyl group;
(ii) $R_2$ comprises an alkynyl group;
(iii) R comprises a terminal group;
(iv) x ranges from 0 to less than 1; and,
(v) n ranges from about 10 to about 1000.

2. The poly(glycolide) polymer of claim 1, wherein the alkynyl group comprises 3 to 12 carbon atoms.

3. The poly(glycolide) polymer of claim 1, wherein the azide-substituted hydrophilic organic compound comprises a compound selected from the group consisting of an azide-substituted polyoxyalkylene, an azide-substituted organic amine, an azide-substituted carboxylic acid, an azide-substituted carboxylate salt, an azide-substituted alkyl polyoxyalkylene, an azide-substituted ketone, an azide-substituted alcohol, an azide-substituted ester, and combinations thereof.

4. The poly(glycolide) polymer of claim 1, wherein the polymer is in the form of a unimolecular micelle having (i) a diameter of about 50 nm or less as measured by dynamic light scattering in aqueous solution with (ii) a substantially hydrophilic exterior and a substantially hydrophobic interior.

5. The poly(glycolide) polymer of claim 4, wherein the unimolecular micelle further-comprises an encapsulated drug within the interior.

6. The poly(glycolide) polymer of claim 4, wherein the triazole reaction product comprises moieties resulting from the reaction of the alkynyl glycolide according to Formula III and the azide-substituted drug.

7. The poly(glycolide) polymer of claim 1, wherein: the triazole reaction product comprises moieties resulting from the reaction of the alkynyl glycolide according to Formula III and the azido organic crosslinker, the polymer is in the form of an intramolecularly crosslinked nanoparticle having (i) a diameter of about 35 nm or less as measured by dynamic light scattering in aqueous solution with (ii) a substantially hydrophilic exterior and a substantially hydrophobic interior.

8. The poly(glycolide) polymer of claim 7, wherein the crosslinked nanoparticle further comprises an encapsulated drug within the interior.

9. The poly(glycolide) polymer of claim 7, wherein the triazole reaction product comprises moieties resulting from the reaction of the alkynyl glycolide according to Formula III and the azide-substituted drug.

10. A plurality of crosslinked nanoparticles according to claim 7, wherein the plurality of crosslinked nanoparticles has a distribution of crosslinking degrees selected to control the rate of release of an encapsulated component or a covalently bound component in the plurality of crosslinked nanoparticles.

* * * * *